(12) United States Patent
Sekiguchi et al.

(10) Patent No.: US 11,959,103 B2
(45) Date of Patent: Apr. 16, 2024

(54) METHOD FOR INDUCING PLURIPOTENT STEM CELLS TO DIFFERENTIATE INTO SOMATIC CELLS

(71) Applicants: OSAKA UNIVERSITY, Osaka (JP); KYOTO UNIVERSITY, Kyoto (JP)

(72) Inventors: Kiyotoshi Sekiguchi, Osaka (JP); Fumi Ebisu, Osaka (JP); Hidetoshi Sakurai, Kyoto (JP); Mingming Zhao, Kyoto (JP); Megumu Saito, Kyoto (JP)

(73) Assignees: OSAKA UNIVERSITY, Osaka (JP); KYOTO UNIVERSITY, Kyoto (JP)

(*) Notice: Subject to any disclaimer, the term of this patent is extended or adjusted under 35 U.S.C. 154(b) by 619 days.

(21) Appl. No.: 16/348,944

(22) PCT Filed: Nov. 9, 2017

(86) PCT No.: PCT/JP2017/040496
§ 371 (c)(1),
(2) Date: May 10, 2019

(87) PCT Pub. No.: WO2018/088501
PCT Pub. Date: May 17, 2018

(65) Prior Publication Data
US 2019/0276804 A1 Sep. 12, 2019

(30) Foreign Application Priority Data
Nov. 11, 2016 (JP) ................................ 2016-220994

(51) Int. Cl.
| | |
|---|---|
| *C12N 5/0735* | (2010.01) |
| *A61K 35/34* | (2015.01) |
| *A61K 35/545* | (2015.01) |
| *A61P 9/00* | (2006.01) |
| *A61P 21/00* | (2006.01) |
| *A61P 43/00* | (2006.01) |
| *C12N 5/071* | (2010.01) |
| *C12N 5/077* | (2010.01) |
| *C12N 5/10* | (2006.01) |

(52) U.S. Cl.
CPC ............ *C12N 5/0657* (2013.01); *A61K 35/34* (2013.01); *A61K 35/545* (2013.01); *A61P 9/00* (2018.01); *A61P 21/00* (2018.01); *A61P 43/00* (2018.01); *C12N 5/0658* (2013.01); *C12N 5/069* (2013.01); *C12N 5/10* (2013.01); *C12N 2501/115* (2013.01); *C12N 2501/12* (2013.01); *C12N 2501/155* (2013.01); *C12N 2501/16* (2013.01); *C12N 2501/165* (2013.01); *C12N 2501/91* (2013.01); *C12N 2501/998* (2013.01); *C12N 2506/45* (2013.01)

(58) Field of Classification Search
CPC .... C12N 5/0657; C12N 5/0658; C12N 5/069; C12N 2506/45
See application file for complete search history.

(56) References Cited

U.S. PATENT DOCUMENTS

| | | |
|---|---|---|
| 9,499,794 B2 | 11/2016 | Tryggvason et al. |
| 2013/0280750 A1 | 10/2013 | Tryggvason et al. |
| 2014/0127806 A1 | 5/2014 | Sekiguchi et al. |
| 2016/0137965 A1 | 5/2016 | Sekiguchi et al. |
| 2016/0215260 A1 | 7/2016 | Takahashi et al. |
| 2017/0067016 A1 | 3/2017 | Tryggvason et al. |
| 2017/0159020 A1 | 6/2017 | Sekiguchi et al. |
| 2018/0208893 A1 | 7/2018 | Nakahata et al. |
| 2018/0362930 A1 | 12/2018 | Tryggvason et al. |
| 2019/0153391 A1 | 5/2019 | Ochi et al. |

FOREIGN PATENT DOCUMENTS

| | | |
|---|---|---|
| WO | 2010/140464 | 12/2010 |
| WO | 2012/137970 | 10/2012 |
| WO | 2013/156855 | 10/2013 |
| WO | 2014/199754 | 12/2014 |
| WO | 2015/004539 | 1/2015 |
| WO | 2016/010082 | 1/2016 |
| WO | 2016/043168 | 3/2016 |
| WO | 2016/108288 | 7/2016 |
| WO | 2018/038242 | 3/2018 |

OTHER PUBLICATIONS

Rufaihah, 2013, Am J Transl Res, 5:21-35.*
Chal, 2015, Nature Biotechnology, 33:962.*
International Preliminary Report on Patentability dated May 16, 2019 in International Application No. PCT/JP2017/040496.
Extended European Search Report dated May 18, 2020 in corresponding European Patent Application No. 17868961.8.
International Search Report dated Feb. 6, 2018 in International Application No. PCT/JP2017/040496.
Kadari, Asifiqbal et al., "Robust Generation of Cardiomyocytes from Human iPS Cells Requires Precise Modulation of BMP and WNT Signaling", Stem Cell Reviews and Reports, 2015, vol. 11, pp. 560-569.
Ohta, Ryo et al., "Laminin-guided highly efficient endothelial commitment from human pluripotent stem cells", Scientific Reports, Nov. 2, 2016, vol. 6, No. 35680.
Seeger, Tanja et al., "Mesenchymal Stromal Cells for Sphincter Regeneration: Role of Laminin Isoforms upon Myogenic Differentiation", PLOS ONE, Sep. 25, 2015, pp. 1-18.

* cited by examiner

*Primary Examiner* — Valarie E Bertoglio
(74) *Attorney, Agent, or Firm* — Wenderoth, Lind & Ponack, L.L.P.

(57) ABSTRACT

Provided is a method for inducing pluripotent stem cells to differentiate into somatic cells in a culture medium containing a heparin binding growth factor, the method comprising bringing cells into contact with a conjugate of a laminin E8 fragment and a growth factor binding domain-containing fragment of a heparan sulfate proteoglycan. According to the present invention, pluripotent stem cells can be induced to differentiate into any desired somatic cells in a highly efficient manner.

9 Claims, 13 Drawing Sheets

Fig. 1
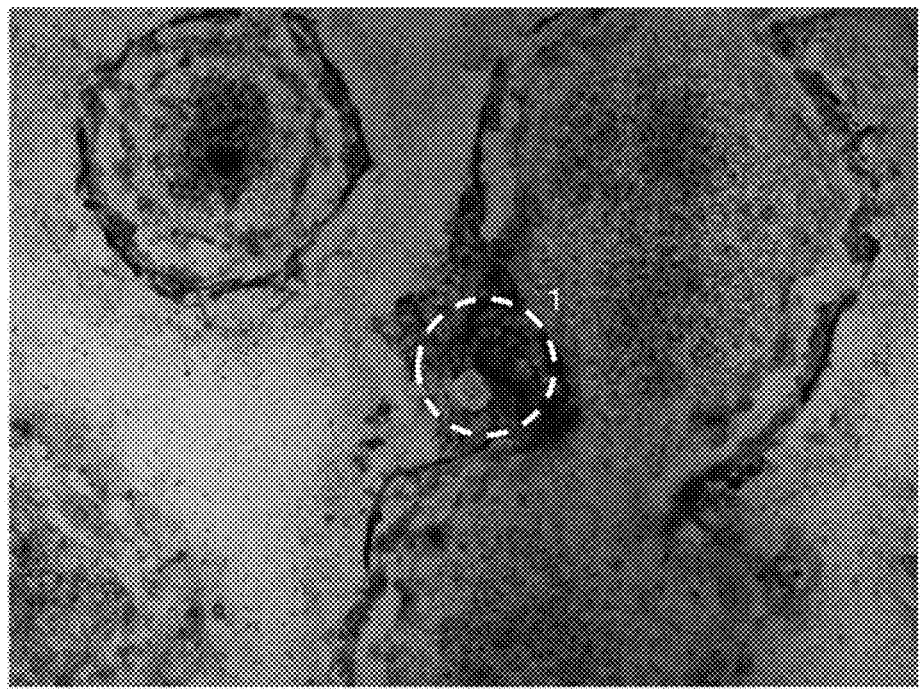
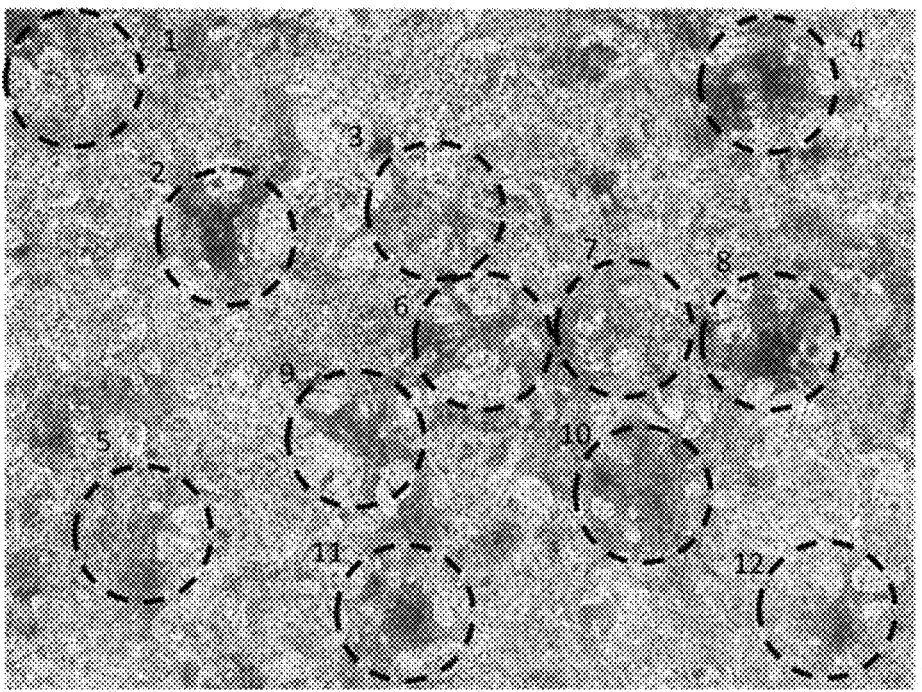

SIX1 (D14)

METHOD FOR INDUCING PLURIPOTENT STEM CELLS TO DIFFERENTIATE INTO SOMATIC CELLS

TECHNICAL FIELD

The present invention relates to a method for inducing pluripotent stem cells to differentiate into somatic cells. More particularly, the present invention relates to a method for inducing pluripotent stem cells to differentiate into somatic cells using a conjugate of a laminin fragment and a growth factor binding domain-containing fragment of a heparan sulfate proteoglycan.

BACKGROUND ART

Human pluripotent stem cells, such as human ES cells and human iPS cells, are receiving worldwide attention for their potential application to regenerative medicine. For practical application of human pluripotent stem cells to regenerative medicine, there is a need to develop techniques for inducing such stem cells to differentiate into somatic cells in a highly efficient and stable manner. A key to successful selective differentiation of human pluripotent stem cells into any desired somatic cells is an appropriate selection of growth factors to be added to a culture medium and of extracellular matrices serving as a scaffold. However, there are no established extracellular matrices to enhance the efficiency of selective differentiation of human pluripotent stem cells into any desired somatic cells.

The present inventors previously found that a modified laminin, which is a conjugate of a laminin E8 fragment and a cell-growth regulatory molecule, such as a growth factor binding molecule, is suitable as an extracellular matrix for maintaining and culturing pluripotent stem cells, such as iPS cells, in an undifferentiated state without affecting their pluripotency; and that the modified laminin is suitable as an extracellular matrix for establishing iPS cells from somatic cells (Patent Literature 1). However, there has been no report that the modified laminin described in Patent Literature 1 has been used as an extracellular matrix for induced differentiation.

CITATION LIST

Patent Literature

Patent Literature 1: WO 2012/137970

SUMMARY OF INVENTION

Technical Problem

An object of the present invention is to find an extracellular matrix which enhances the efficiency of selective differentiation of pluripotent stem cells into any desired somatic cells and to provide a highly efficient method for induced differentiation using the extracellular matrix.

Solution to Problem

In order to achieve the above-mentioned object, the present invention includes the following.
[1] A method for inducing pluripotent stem cells to differentiate into somatic cells in a culture medium containing a heparin binding growth factor, the method comprising bringing cells into contact with a conjugate of a laminin E8 fragment and a growth factor binding domain-containing fragment of a heparan sulfate proteoglycan.
[2] The method according to the above [1], wherein the growth factor binding domain-containing fragment of a heparan sulfate proteoglycan is a perlecan domain 1-containing fragment.
[3] The method according to the above [1] or [2], wherein the conjugate has a structure in which the growth factor binding domain-containing fragment of a heparan sulfate proteoglycan is conjugated to the α chain C-terminus of the laminin E8 fragment.
[4] The method according to any of the above [1] to [3], wherein a cell culture vessel coated with the conjugate is used for inducing pluripotent stem cells to differentiate into somatic cells.
[5] The method according to any of the above [1] to [4], wherein the heparin binding growth factor is one or more kinds selected from bone morphogenetic protein 2, bone morphogenetic protein 4, bone morphogenetic protein 7, basic fibroblast growth factor, fibroblast growth factor 4, fibroblast growth factor 8, fibroblast growth factor 10, hepatocyte growth factor, platelet-derived growth factor-BB, Wnt3a protein, sonic hedgehog, vascular endothelial growth factor, transforming growth factor-β, activin A, oncostatin M, keratinocyte growth factor and glial cell-derived neurotrophic factor.
[6] The method according to any of the above [1] to [5], wherein the pluripotent stem cells are human iPS cells.
[7] The method according to any of the above [1] to [6], wherein the somatic cells are mesoderm-derived somatic cells.
[8] The method according to any of the above [1] to [7], wherein human iPS cells are induced to differentiate into cardiomyocytes in a culture medium containing bone morphogenetic protein 4 or activin A, and wherein cells are brought into contact with a conjugate in which perlecan domain 1 is conjugated to the α chain C-terminus of a human laminin α4β2γ1 E8 fragment or the α chain C-terminus of a human laminin α5β1γ1 E8 fragment.
[9] The method according to any of the above [1] to [7], wherein human iPS cells are induced to differentiate into skeletal muscle cells in a culture medium containing basic fibroblast growth factor and hepatocyte growth factor, and wherein cells are brought into contact with a conjugate in which perlecan domain 1 is conjugated to the α chain C-terminus of a human laminin α4β2γ1 E8 fragment, the α chain C-terminus of a human laminin α5β1γ1 E8 fragment, the α chain C-terminus of a human laminin α4β1γ1 E8 fragment, or the α chain C-terminus of a human laminin α5β2γ1 E8 fragment.
[10] The method according to any of the above [1] to [7], wherein human iPS cells are induced to differentiate into vascular endothelial cells in a culture medium containing vascular endothelial growth factor, and wherein cells are brought into contact with a conjugate in which perlecan domain 1 is conjugated to the α chain C-terminus of a human laminin α4β1γ1 E8 fragment.

Advantageous Effects of Invention

The present invention provides a method for inducing pluripotent stem cells to differentiate into any desired somatic cells in a highly efficient manner.

BRIEF DESCRIPTION OF DRAWINGS

FIGS. 1A and 1B are still frames from separate 10-second movies of beating cell cluster(s) obtained by induced differentiation of human iPS cells (253G1 cell line) into cardiomyocytes. FIG. 1A shows the results for the cells obtained by induced differentiation on a plate coated with a human laminin α5β1γ1 E8 fragment. FIG. 1B shows the results for the cells obtained by induced differentiation on a plate coated with a conjugate in which human perlecan domain 1 is fused to the α5 chain C-terminus of a human laminin α5β1γ1 E8 fragment.

FIG. 4A shows the results for the cells on a plate coated with a human laminin α5β1γ1 E8 fragment. FIG. 4B shows the results for the cells on a plate coated with a conjugate in which human perlecan domain 1 is fused to the α5 chain C-terminus of a human laminin α5β1γ1 E8 fragment.

FIG. 5A shows the results for the cells on a plate coated with a human laminin α4β2γ1 E8 fragment. FIG. 5B shows the results for the cells on a plate coated with a conjugate in which human perlecan domain 1 is fused to the α4 chain C-terminus of a human laminin α4β2γ1 E8 fragment.

FIG. 7A shows the results for the SIX1 gene, and FIG. 7B shows the results for the Sox1 gene.

FIG. 10A shows the results for the MyoD gene, FIG. 10B shows the results for the MHC gene, FIG. 10C shows the results for the myogenin gene, and FIG. 10D shows the results for the Pax7 gene.

FIG. 12A shows the results for the SIX1 gene, and FIG. 12B shows the results for the DMRT2 gene.

DESCRIPTION OF EMBODIMENTS

Figure 2:
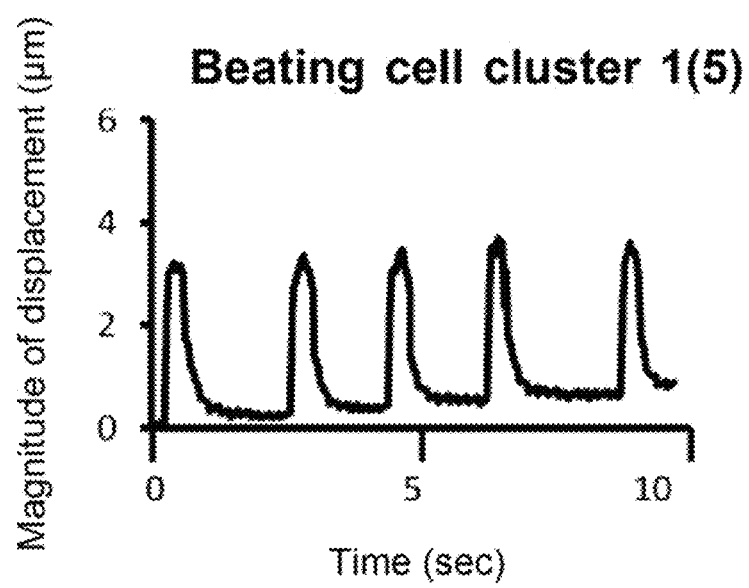
FIG. 2 graphically illustrates the number of beats and the magnitude of displacement of the beating cell cluster of FIG. 1A in 10 seconds.

The present invention provides a method for inducing pluripotent stem cells to differentiate into somatic cells in a highly efficient manner. The method of the present invention for induced differentiation (hereinafter referred to as "the method of the present invention") is characterized by bringing cells into contact with a conjugate of a laminin E8 fragment and a growth factor binding domain-containing fragment of a heparan sulfate proteoglycan. The method of the present invention can be applied to a method for inducing pluripotent stem cells to differentiate into somatic cells in a culture medium containing a heparin binding growth factor.

Laminin is a heterotrimeric molecule consisting of three subunits termed α, β and γ chains. Five kinds of α chains (α1 to α5), three kinds of β chains (β1 to β3) and three kinds of γ chains (γ1 to γ3) are known, and various combinations of these chains result in at least 12 kinds of laminin isoforms (see Table 1). As used herein, each laminin isoform is written in abbreviation, for example, "laminin 111".

TABLE 1

| α chain | Trimer composition | |
|---|---|---|
| α1 | α1β1γ1 | (laminin-1) |
|    | α1β2γ1 | (laminin-3) |
| α2 | α2β1γ1 | (laminin-2) |
|    | α2β2γ1 | (laminin-4) |
|    | α2β1γ3 | (laminin-12) |
| α3 | α3β3γ2 | (laminin-5) |
|    | α3β1γ1 | (laminin-6) |
|    | α3β2γ1 | (laminin-7) |
| α4 | α4β1γ1 | (laminin-8) |
|    | α4β2γ1 | (laminin-9) |
| α5 | α5β1γ1 | (laminin-10) |
|    | α5β2γ1 | (laminin-11) |

The laminin E8 fragment (hereinafter referred to as "laminin E8" or "E8"), which is a heterotrimeric fragment obtained by elastase digestion of mouse laminin 111, was identified as having strong cell-adhesive activity (Edgar D et al., J. Cell Biol., 105: 589-598, 1987). Elastase digestion of laminins other than mouse laminin 111 could presumably produce fragments corresponding to the mouse laminin 111E8, but there has been no report on isolation or identification of such E8 fragments. Therefore, the laminin E8 used in the method of the present invention does not have to be an elastase-digestion product of laminins, and may be any laminin fragment equivalent in cell-adhesive activity and structure to the mouse laminin 111E8.

Laminin E8 is a trimeric fragment composed of a C-terminal fragment of the α chain lacking globular domains 4 and 5 (hereinafter referred to as "α chain E8"), a C-terminal fragment of the β chain (hereinafter referred to as "β chain E8"), and a C-terminal fragment of the γ chain (hereinafter referred to as "γ chain E8"). The molecular weight of the trimer is not particularly limited, but is usually about 150 to 170 kDa. The glutamic acid residue at the 3rd position from the C-terminus of the γ chain E8 is essential for the integrin binding activity of laminin E8 (Hiroyuki Ido et al., The Journal of Biological Chemistry, 282, 11144-11154, 2007).

The laminin E8 may be from laminins of any organism, and is preferably from laminins of mammals. Examples of the mammal include but are not limited to humans, mice, rats, cattle and pigs. Usually, the laminin E8 is from laminins of an animal species that is the origin of the pluripotent stem cells to be used. In the method of the present invention, human pluripotent stem cells and E8 from human laminins are particularly preferably used. This is because, when cells for use in human regenerative medicine are prepared by induced differentiation of pluripotent stem cells, its process requires no use of xenogeneic components.

The laminin E8 can be produced by appropriate known recombinant techniques, for example, by preparing DNAs encoding the α chain E8, the β chain E8 and the γ chain E8, inserting the DNAs into separate expression vectors, co-introducing the three resulting expression vectors into appropriate host cells, and purifying the expressed trimeric protein by a known method. The production method of the laminin E8 may be, for example, the method of Ido et al. (Hiroyuki Ido et al., The Journal of Biological Chemistry, 282, 11144-11154, 2007), but is not limited thereto. The laminin E8 may be a modified laminin E8 that has modification of one or more amino acid residues but retains biological activities of the native laminin E8.

Information regarding the nucleotide sequences of the genes encoding laminin α, β and γ chains of major mammals and the amino acid sequences of these chains can be obtained from known databases (e.g., GenBank etc.). The accession numbers of the constituent chains of human laminins are shown in Table 2. Information regarding the nucleotide and amino acid sequences of the constituent chains of laminins of other organisms can also be obtained from known databases (e.g., GenBank etc.).

TABLE 2

| | Amino acid sequence | Nucleotide sequence |
|---|---|---|
| Human laminin α1 chain | NP_005550 | NM_005559 |
| Human laminin α2 chain | NP_000417 | NM_000426 |
| Human laminin α3 chain | NP_000218 | NM_000227 |
| Human laminin α4 chain | NP_002281 | NM_002290 |
| Human laminin α5 chain | NP_005551 | NM_005560 |
| Human laminin β1 chain | NP_002282 | NM_002291 |
| Human laminin β2 chain | NP_002283 | NM_002292 |
| Human laminin β3 chain | NP_000219 | NM_000228 |
| Human laminin γ1 chain | NP_002284 | NM_002293 |
| Human laminin γ2 chain | NP_005553 | NM_005562 |
| Human laminin γ3 chain | NP_006050 | NM_006059 |

Examples of the heparan sulfate proteoglycan used for the conjugate with the laminin E8 include perlecan, agrin, type XVIII collagen, syndecans 1 to 4 and glypicans 1 to 6. Examples of the growth factor binding domain-containing fragment of a heparan sulfate proteoglycan include perlecan domain 1 (D1: $Gly^{25}$-$Pro^{196}$) and a region containing follistatin (FS) domains 1 to 8 of agrin (Winzen et al., The Journal of Biological Chemistry, 278, 30106-30114, 2003). Preferred is perlecan domain 1.

The production method of the heparan sulfate proteoglycan or a growth factor binding domain-containing fragment thereof is not particularly limited, and these can be produced by appropriate known recombination techniques. Information regarding the nucleotide sequences of human genes encoding perlecan, agrin, type XVIII collagen, syndecans 1 to 4 and glypicans 1 to 6, and the amino acid sequences of these heparan sulfate proteoglycans can be obtained from known databases (e.g., GenBank etc.) with the respective accession numbers shown in Table 3.

TABLE 3

| | Amino acid sequence | Nucleotide sequence |
|---|---|---|
| Human perlecan | NP_005520 | NM_005529 |
| Human agrin | NP_940978 | NM_198576 |
| Human type XVIII collagen α1 chain | NP_085059 | NM_030582 |
| Human syndecan 1 | NP_001006947 | NM_001006946 |
| Human syndecan 2 | NP_002989 | NM_002998 |
| Human syndecan 3 | NP_055469 | NM_014654 |
| Human syndecan 4 | NP_002990 | NM_002999 |
| Human glypican 1 | NP_002072 | NM_002081 |
| Human glypican 2 | NP_689955 | NM_152742 |
| Human glypican 3 | NP_001158089 | NM_001164617 |
| Human glypican 4 | NP_001439 | NM_001448 |
| Human glypican 5 | NP_004457 | NM_004466 |
| Human glypican 6 | NP_005699 | NM_005708 |

In the conjugate of a laminin E8 and a growth factor binding domain-containing fragment of a heparan sulfate proteoglycan, the growth factor binding domain-containing fragment of a heparan sulfate proteoglycan (hereinafter referred to as "the growth factor binding domain-containing fragment") is preferably conjugated to at least one site selected from the α chain N-terminus, the α chain C-terminus, the chain N-terminus and the γ chain N-terminus of the laminin E8. The growth factor binding domain-containing fragment may be conjugated to 2, 3 or 4 sites of the laminin E8. The site to which the growth factor binding domain-containing fragment is conjugated is not particularly limited, but is preferably the α chain C-terminus of the laminin E8. The term. "conjugate" may be referred to as a conjugate, a complex, a composite, etc. in Japanese. Hereinafter, the conjugate of the laminin E8 and the growth factor binding domain-containing fragment is referred to simply as "the conjugate".

In the conjugate, the laminin E8 and the growth factor binding domain-containing fragment may be conjugated directly or via a linker. The linker may be any known linker usable for conjugation of proteins. Alternatively, the conjugate may be in the form of a fusion protein of the laminin E8 and the growth factor binding domain-containing fragment. For example, for production of a conjugate in which the growth factor binding domain-containing fragment is fused to the α chain C-terminus of the laminin E8, firstly, a DNA encoding the α chain E8 and a DNA encoding the growth factor binding domain-containing fragment are combined into a fusion gene, and the fusion gene is ligated into an expression vector. Subsequently, this expression vector, an expression vector for human laminin β chain E8 and an expression vector for human laminin γ chain E8, that is, three different expression vectors, are co-transfected into appropriate host cells, and the expressed trimeric protein is purified by a known method. Similarly, conjugates in which the growth factor binding domain-containing fragment is conjugated to a site (chain terminus) other than the α chain C-terminus of the laminin E8 and conjugates in which the growth factor binding domain-containing fragments are conjugated to more than one site (chain terminus) of the laminin E8 can be produced.

In the method of the present invention, the contact of the cells with the conjugate can be achieved by culturing the cells in a culture medium supplemented with the conjugate or by culturing the cells in a culture vessel coated with the conjugate. In the case where a culture medium supplemented with the conjugate is used, the conjugate may be added to a medium in advance or just before use. The amount of the conjugate added is not particularly limited, and is preferably about 0.03 to 25 µg, more preferably about 0.06 to 10 µg, and still more preferably about 0.1 to 2 µg per $cm^2$ of the culture surface area of a culture vessel.

In the case of coating a culture vessel with the conjugate, the following procedure can be employed for coating. Firstly, the conjugate is diluted with a suitable solvent, such as PBS, physiological saline or a physiological saline adjusted to a neutral pH with tris(hydroxymethyl)aminomethane or 4-(2-hydroxyethyl)-1-piperazine ethanesulfonic acid. Then, the diluted solution is added to a suitable culture vessel, and the culture vessel is allowed to stand at room temperature to about 37° C. for about 1 to 12 hours. The coating concentration of the conjugate is not particularly limited, and is preferably about 0.03 to 25 µg, more preferably about 0.06 to 10 µg, and still more preferably about 0.1 to 2 µg per $cm^2$ of the culture surface area of the culture vessel. When a culture vessel is coated with the conjugate together with gelatin, serum albumin, and/or the like as a substance capable of preventing reduction in the activity of the conjugate, drying-caused reduction in the activity of the conjugate attached on the culture vessel can be prevented (see WO 2014/199754 A1).

In the method of the present invention, the duration of the contact of the cells with the conjugate is not particularly limited. The duration of the contact of the cells with the conjugate may be part of the induction period of differentiation of pluripotent stem cells into somatic cells and need not be the whole induction period.

The heparin binding growth factor contained in the culture medium for induced differentiation of pluripotent stem cells into somatic cells is not particularly limited, and examples include bone morphogenetic protein 2 (BMP2), bone morphogenetic protein 4 (BMP4), bone morphogenetic protein 7 (BMP7), basic fibroblast growth factor (bFGF, also referred to as fibroblast growth factor 2 (FGF2)), fibroblast growth factor 4 (FGF4), fibroblast growth factor 8 (FGF8), fibroblast growth factor 10 (FGF10), hepatocyte growth factor (HGF), platelet-derived growth factor-BB (PDGF-BB), Wnt3a protein (Wnt3a), sonic hedgehog (Shh), vascular endothelial growth factor (VEGF), transforming growth factor-β (TGF-β), activin A, oncostatin M (OSM), keratinocyte growth factor (KGF, also referred to as fibroblast growth factor 7 (FGF7)) and glial cell-derived neurotrophic factor (GDNF). The heparin binding growth factor may be added to a culture medium or secreted from the cells cultured in a culture medium. The heparin binding growth factor contained in the culture medium may be of one kind or a combination of two or more kinds. The method of the present invention facilitates the binding of the laminin E8 of the conjugate to cell-surface integrins, and also facilitates the binding of the heparin binding growth factor contained in the culture medium to the growth factor binding domain of the growth factor binding domain-containing fragment conjugated to the laminin E8, resulting in efficient activation of cell-surface growth factor receptors. Therefore, the method of the present invention is expected to achieve high efficiency of differentiation into somatic cells.

The pluripotent stem cells that can be used in the method of the present invention are stem cells which have pluripotency, i.e., the ability to differentiate into any type of cells present in a living body, and also have proliferative capacity. Examples of the stem cells include embryonic stem cells (ES cells), embryonic stem cells from a cloned embryo obtained by nuclear transfer (ntES cells), spermatogenic stem cells (GS cells), embryonic germ cells (EG cells), induced pluripotent stem cells (iPS cells), and pluripotent cells from cultured fibroblasts or myeloid stem cells (Muse cells). Preferred are ES cells, ntES cells and iPS cells, and more preferred are iPS cells. The pluripotent stem cells are preferably pluripotent stem cells of mammals. The mammal is not particularly limited, and examples include humans, mice, rats, cattle and pigs. Particularly preferred are humans. With the use of human pluripotent stem cells, somatic cells safe and compatible for use in human regenerative medicine can be obtained.

The isoform of the laminin E8 of the conjugate is preferably selected as appropriate for the types of integrins expressed in the cells during the course of differentiation and in terminally differentiated mature cells. Examples of a laminin isoform having binding specificity to integrin α6β1 include laminins having an α5 chain (laminin 511, laminin 521), laminins having an α3 chain (laminin 311, laminin 321, laminin 332), laminins having an α4 chain (laminin 411, laminin 421) and laminins having an α1 chain (laminin 111, laminin 121). Examples of a laminin isoform having binding specificity to integrin α6134 include laminins having an α3 chain (laminin 332, laminin 311, laminin 321) and laminins having an α5 chain (laminin 511, laminin 521). Examples of a laminin isoform having binding specificity to integrin α3β1 include laminins having an α3 chain (laminin 332, laminin 311, laminin 321) and laminins having an α5 chain (laminin 511, laminin 521). Examples of a laminin isoform having binding specificity to integrin α7131 include laminins having an α2 chain (laminin 211, laminin 221) and laminins having an α1 chain (laminin 111, laminin 121).

In the method for inducing pluripotent stem cells to differentiate into any desired somatic cells in a culture medium containing a heparin binding growth factor, exemplary suitable combinations of the somatic cells and the heparin binding growth factor are shown in Table 4. The scope of the present invention is not limited thereto, and the present invention can be applied to any method for inducing pluripotent stem cells to differentiate into any desired somatic cells in a culture medium containing a heparin binding growth factor.

TABLE 4

| | Somatic cells | Heparin binding growth factor |
|---|---|---|
| 1 | Cardiomyocytes | BMP4 |
| 2 | Cardiomyocytes | BMP4, activin A |
| 3 | Skeletal muscle cells | bFGF, HGF |
| 4 | Vascular endothelial cells | VEGF |
| 5 | Hepatocytes | activin A, Wnt3a, HGF, OSM |
| 6 | Corneal cells | KGF, bFGF |
| 7 | Pancreatic progenitor cells | activin A, KGF |
| 8 | Insulin-producing cells | Wnt3a, activin A, FGF10 |
| 9 | Chondrocytes | PDGF-BB, TGF-β3, BMP4 |
| 10 | Chondrocytes | Wnt3a, activin A, BMP2, TGF-β1, bFGF |
| 11 | Dopamine-producing neurons | FGF8, GDNF |
| 12 | Renal progenitor cells | Wnt3a, activin A, BMP7 |
| 13 | Motor neurons | bFGF, Shh, GDNF |
| 14 | Hematocytes | BMP4, VEGF |

The combinations of the somatic cells and the heparin binding growth factor shown in Table 4 are described in the literature, and representative references are given below.
(1) Example 1 in the present specification
(2) Yang L et al., Nature, 2008 May 22; 453(7194):524-8, doi: 10.1038/nature06894, Epub 2008 Apr. 23.
(3) WO 2016/108288 A1
(4) Ohta R et al., Scientific Reports, 2016 Nov. 2; 6:35680, doi: 10.1038/srep35680.
(5) Cameron K et al., Stem Cell Reports, 2015 Dec. 8; 5:1250-1262. doi: 10.1016/j.stemcr.2015.10.016. Epub 2015 Nov. 25.
(6) Hayashi et al., Nature. 2016 Mar. 17; 531 (7594):376-80. doi: 10.1038/nature17000. Epub 2016 Mar. 9.
(7) Toyoda T et al., Stem Cell Res. 2015 March; 14 (2): 185-97. doi: 10.1016/j.scr.2015.01.007. Epub 2015 Jan. 28.
(8) Thatava T et al., Gene Ther. 2011 March; 18(3):283-93. doi: 10.1038/gt.2010.145. Epub 2010 Nov. 4.
(9) Fukuta M et al., PLoS One. 2014 Dec. 2; 9(12):e112291. doi: 10.1371/journal.pone.0112291. eCollection 2014.
(10) Kimura T et al., TISSUE ENGINEERING: Part A Volume 22, Numbers 23 and 24, 2016. DOI: 10.1089/ten.tea.2016.0189
(11) Doi D et al., Stem Cell Reports. 2014 Mar. 6; 2(3): 337-50. doi: 10.1016/j.stemcr.2014.01.013. eCollection 2014.
(12) Mae S et al., Nat Commun. 2013; 4:1367. doi: 10.1038/ncomms2378.
(13) Egawa N et al., Sci Transl Med. 2012 Aug. 1; 4 (145):145ra104. doi: 10.1126/scitranslmed.3004052.
(14) Niwa A et al., PLoS One. 2011; 6(7):e22261. doi: 10.1371/journal.pone.0022261. Epub 2011 Jul. 27.

The somatic cells as the differentiated cells obtainable by the method of the present invention are not particularly limited and can be any somatic cells that can be derived by differentiation of pluripotent stem cells. Specific examples include ectoderm-derived cells such as corneal cells, dopamine-producing neurons, motor neurons, peripheral neurons, pigment epithelial cells, skin cells and inner ear cells. Also included are entoderm-derived cells such as hepatocytes, pancreatic progenitor cells, insulin-producing cells, cholangiocytes, alveolar epithelial cells and intestinal epithelial cells. Also included are mesoderm-derived cells such as cardiomyocytes, skeletal muscle cells, vascular endothelial cells, hepatocytes, osteocytes, chondrocytes, renal progenitor cells and renal epithelial cells. The somatic cells include not only terminally differentiated mature cells but also cells which are in the middle of differentiation and have yet to terminally differentiate.

The somatic cells as the differentiated cells obtainable by the method of the present invention may be mesoderm-derived somatic cells. The somatic cells in the method of the present invention may be mesoderm-derived muscle cells, or mesoderm-derived cardiomyocytes or skeletal muscle cells. The somatic cells in the method of the present invention may be mesoderm-derived vascular endothelial cells.

The method of the present invention can be employed for inducing human iPS cells to differentiate into cardiomyocytes in a culture medium containing bone morphogenetic protein 4 or activin A. In this case, the conjugate used is preferably a conjugate in which perlecan domain 1 is conjugated to the α4 chain C-terminus of human laminin 421E8 or the α5 chain C-terminus of human laminin 511E8.

In the case of inducing human iPS cells to differentiate into cardiomyocytes by the method of the present invention, cells are preferably in contact with the conjugate throughout the induction period of differentiation. The bone morphogenetic protein 4 or activin A is preferably added to a culture medium at the initiation of the induced differentiation. After culture for about 24 hours, the culture medium is preferably replaced with a culture medium without bone morphogenetic protein 4 or activin A.

The method of the present invention can be employed for inducing human iPS cells to differentiate into skeletal muscle cells in a culture medium containing basic fibroblast growth factor and hepatocyte growth factor. In this case, the conjugate used is preferably a conjugate in which perlecan domain 1 is conjugated to the α4 chain C-terminus of human laminin 421E8, the α5 chain C-terminus of human laminin 511E8, the α4 chain C-terminus of human laminin 411E8 or the α5 chain C-terminus of human laminin 521E8. More preferred is a conjugate in which perlecan domain 1 is conjugated to the α4 chain C-terminus of human laminin 421E8.

In the case of inducing human iPS cells to differentiate into skeletal muscle cells by the method of the present invention, cells are preferably in contact with the conjugate throughout the induction period of differentiation. The basic fibroblast growth factor and hepatocyte growth factor are preferably added to a culture medium after differentiation of the human iPS cells into dermomyotome.

The method of the present invention can be employed for inducing human iPS cells to differentiate into vascular endothelial cells in a culture medium containing vascular endothelial growth factor. In this case, the conjugate used is preferably a conjugate in which perlecan domain 1 is conjugated to the α4 chain C-terminus of human laminin 411E8.

In the case of inducing human iPS cells to differentiate into vascular endothelial cells by the method of the present invention, it is preferable that inducing the human iPS cells to differentiate into mesodermal progenitor cells is followed by bringing the mesodermal progenitor cells into contact with the conjugate. The vascular endothelial growth factor is preferably added to a culture medium at the initiation of contact of the cells with the conjugate.

EXAMPLES

Hereinafter, the present invention will be described in more detail by Examples, but the present invention is not limited thereto.

Example 1

Examination of the Usefulness of a Conjugate of Laminin E8 and Perlecan Domain 1 in Induced Differentiation of Human iPS Cells into Cardiomyocytes
Experimental Materials and Methods
(1) Laminin E8s and Conjugates of Laminin E8 and Perlecan Domain 1

Human laminin 511E8 (hereinafter referred to as "LN511E8"), a conjugate in which human perlecan domain 1 was fused to the α5 chain C-terminus of LN511E8 (hereinafter referred to as "P-511E8(D1; a-C)"), human laminin 421E8 (hereinafter referred to as "LN421E8"), and a conjugate in which human perlecan domain 1 was fused to the α4 chain C-terminus of LN421E8 (hereinafter referred to as "P-421E8(D1; a-C)") were used. The LN511E8 was prepared as previously described by Ido et al. (Hiroyuki Ido et al., J. Biol. Chem., 282, 11144-11154, 2007) (see Examples in WO 2014/199754 A1). The P-511E8(D1; a-C) was the same molecule as the "Plus#5 laminin E8" described in Examples of WO 2014/199754 A1. Its preparation method is as described in WO 2014/199754 A1. The LN421E8 was prepared as previously described by Ido et al. (loc. cit.) except for using α4 chain E8 and β2 chain E8 instead of α5 chain E8 and pi chain E8, respectively. The preparation methods of an α4 chain E8 expression vector and a β2 chain E8 expression vector are as described in WO 2014/103534 A1. The P-421E8(D1; a-C) was prepared as described in the preparation method of P-511E8(D1; a-C) except for using α4 chain E8 and β2 chain E8 instead of α5 chain E8 and pi chain E8, respectively.

(2) Human iPS Cells

The human iPS cells (hereinafter referred to as "hiPS cells") used were human iPS cell lines 253G1 and 201B7, which were purchased from RIKEN BRC. The hiPS cells were maintained according to a partially modified version of the protocol of Nakagawa et al. (Nakagawa et al., Sci. Rep. 4:3594, doi:10.1038/srep03594, 2014). The 253G1 cell line was seeded on a plate coated with LN511E8 or P-511E8(D1; a-C) prior to induced differentiation. The 201B7 cell line was seeded on a plate coated with LN421E8 or P-421E8(D1; a-C) prior to induced differentiation.

(3) Pre-Culture of hiPS Cells

A cell detachment solution (TrypLE Select (Life Technologies) diluted 1:1 with 0.5 mM EDTA/PBS(−)) was added to the hiPS cells maintained, followed by incubation at 37° C. for 5 minutes. The hiPS cells were detached, and a hiPS cell suspension was prepared. More specifically, after the incubation, the cell detachment solution was aspirated off, and the cells were washed with PBS(−). Then, StemFit AK02N medium (Ajinomoto) containing a ROCK inhibitor (Y-27632, Wako Pure Chemical Industries, Ltd.) at 10 μM was added in a volume of 1 mL/well, and the hiPS cells were harvested using a cell scraper. The hiPS cells were dissociated into single cells by repeated pipetting and then counted using the Countess automated cell counter (Life Technologies).

On the previous day, 6-well culture plates (BD biosciences) were coated by adding 1.5 mL/well of a coating solution containing 22 nM P-511E8 (D1; a-C), 22 nM P-421E8 (D1; a-C), 22 nM LN511E8, or 22 nM LN421E8, and the plates were allowed to stand at 4° C. overnight. On the initial day of pre-culture, a 1 mg/mL solution of recombinant human serum albumin (Novozymes) in PBS(−) was added in a volume of 1.5 mL/well to prevent drying-caused inactivation of the laminin E8s attached on the plates.

The solution in each well was aspirated off, the 253G1 hiPS cells and the 201B7 hiPS cells dissociated as single cells were seeded at $5.0 \times 10^5$ cells/well, and pre-culture was started. The culture medium used was StemFit AK02N medium containing a ROCK inhibitor (Y-27632) at 10 μM. The pre-culture was performed under the conditions of 37° C. and 0.5% $CO_2$ for 3 days. Differentiation was induced at 50 to 60% confluency.

(4) Induced Differentiation into Cardiomyocytes

For inducing the hiPS cells to differentiate into cardiomyocytes, a partially modified version of the protocol of Kadari et al. (Kadari et al., Stem Cell Rev and Rep (2015) 11:560-569) was used. The culture medium and additives used for the induced differentiation are shown in Table 5 below.

TABLE 5

| Day of differentiation | Medium | Additive |
| --- | --- | --- |
| D0 (initial) | RPMI1640 supplemented with B27 supplement, 2 mM L-glutamine and 50 μg/mL L-ascorbic acid | 25 ng/mL BMP4 5 μM CHIR99021 |
| D1 | RPMI1640 supplemented with B27 supplement, 2 mM L-glutamine and 50 μg/mL L-ascorbic acid | 5 μM CHIR99021 |

TABLE 5-continued

| Day of differentiation | Medium | Additive |
|---|---|---|
| D2 | RPMI1640 supplemented with B27 supplement (−) insulin and 2 mM L-glutamine | |
| D3-D4 | RPMI1640 supplemented with B27 supplement (−) insulin and 2 mM L-glutamine | 10 μM IWR1 |
| D5-D6 | RPMI1640 supplemented with B27 supplement (−) insulin and 2 mM L-glutamine | 10 μM IWR1 |
| D7 | RPMI1640 supplemented with B27 supplement and 2 mM L-glutamine | |

On the initial day of induced differentiation (Day 0), BMP4 (final concentration: 25 ng/mL, R&D Systems) and the canonical Wnt signal activator CHIR99021 (final concentration: 5 μM, Sigma-Aldrich) were added to RPMI1640 (Life Technologies) supplemented with B27 supplement (1:50, Life Technologies), 2 mM L-glutamine (Life Technologies) and 50 μg/mL L-ascorbic acid (Sigma-Aldrich), and this culture medium was used. Twenty-four hours later (Day 1), the culture medium was replaced with the same one without BMP4 (still containing 5 μM (final concentration) CHIR99021). Further 24 hours later (Day 2), the culture medium was replaced with RPMI1640 supplemented with B27 supplement (−) insulin (1:50, Life Technologies) and 2 mM L-glutamine. Further 24 hours later (Day 3), the culture medium was replaced with the same one as used on Day 2 except for containing the canonical Wnt signal inhibitor IWR1 (Wako Pure Chemical Industries, Ltd.) at a final concentration of 10 μM. On Day 5, the culture medium was replaced with the same one as used on Day 3. On Day 7, the culture medium was replaced with RPMI1640 supplemented with B27 supplement and 2 mM L-glutamine. Afterwards, the culture medium was replaced with the same one every other day until beating cells were detected by observation (Day 12 at most).

(5) Observation of Beating Cells

The beating behavior of the differentiated cells from the 253G1 hiPS cells was observed. The entire area of each well was observed with a low-magnification (4-fold magnification) lens of the Primovert inverted microscope (ZEISS) to locate beating cell clusters. Next, the beating cell clusters were recorded as a movie for 10 seconds using the time-lapse module of the BZ-X700 all-in-one fluorescence microscope (Keyence) at the same magnification as above (4-fold magnification). Using the Motion Analyzer of the Keyence BZ-X700 all-in-one fluorescence microscope, the 10-second movie was converted into 291 still images, a spot exhibiting contraction and relaxation motions was selected from each beating cell cluster, and the magnitude of displacement due to beating (amplitude: μm) was quantitatively measured. The data were exported to Excel and graphically represented.

(6) FACS Analysis

FACS analysis was performed according to a partially modified version of the method of Yamada et al. (Yamada et al., Biochem J. 2008 Nov. 1; 415(3):417-427). The differentiated cells from the 253G1 hiPS cells and the differentiated cells from the 201B7 hiPS cells were subjected to FACS analysis. A mouse anti-troponin T antibody (clone 1C11, Abcam) was used as a primary antibody, and an Alexa Fluor 488-labeled goat anti-mouse IgG antibody was used as a secondary antibody.

(6-1) FACS Analysis of Differentiated Cells from 253G1 hiPS Cells

The cells after 12-day induction of differentiation were detached with a cell detachment solution (TrypLE Select (Life Technologies) diluted 1:1 with 0.5 mM EDTA/PBS(−)) and dissociated into single cells by repeated pipetting. The cells were fixed in formalin diluted with PBS(−) (formalin:PBS(−)=1:10) at room temperature for 10 minutes. After the formalin was removed, the cells were washed twice with PBS(−) and suspended in 800 μL of PBS(−).

For cell permeabilization, 200 μL of this cell suspension was treated with 200 μL of PBS(−) containing 0.1% Triton X-100 for 15 minutes. After the supernatant was aspirated off, 500 μL of PBS(−) containing 1.5% fetal bovine serum (FBS, Life Technologies) (blocking solution) was added, and the cells were allowed to stand for 15 minutes. After blocking, 1 μL of a mouse anti-troponin T antibody diluted to 4 μg/mL with the blocking solution was added, and the cells were incubated at room temperature for 60 minutes.

After the completion of primary antibody reaction, the cells were washed twice with PBS(−). A secondary antibody (Alexa Fluor 488-labeled goat anti-mouse IgG antibody) diluted 500-fold with PBS(−) was added, and the cells were incubated at room temperature for 60 minutes. After that, the cells were washed twice with 500 μL of PBS(−) and then resuspended in 500 μL of PBS(−). The cell suspension was analyzed for troponin T-positive cells using the FACScan flow cytometer (Becton Dickinson).

(6-2) FACS Analysis of Differentiated Cells from 201B7 hiPS Cells

The cells after 10-day induction of differentiation were used. As described in the above (6-1), the cells were detached, dissociated, fixed and washed. The cells were suspended in 400 μL of PBS(−), and 200 μL of the cell suspension was subjected to primary antibody reaction and secondary antibody reaction as described in (6-1), followed by analysis for troponin T-positive cells using the FACScan flow cytometer (Becton Dickinson).

Results (1) Observation of Beating Cells

Figure 3:
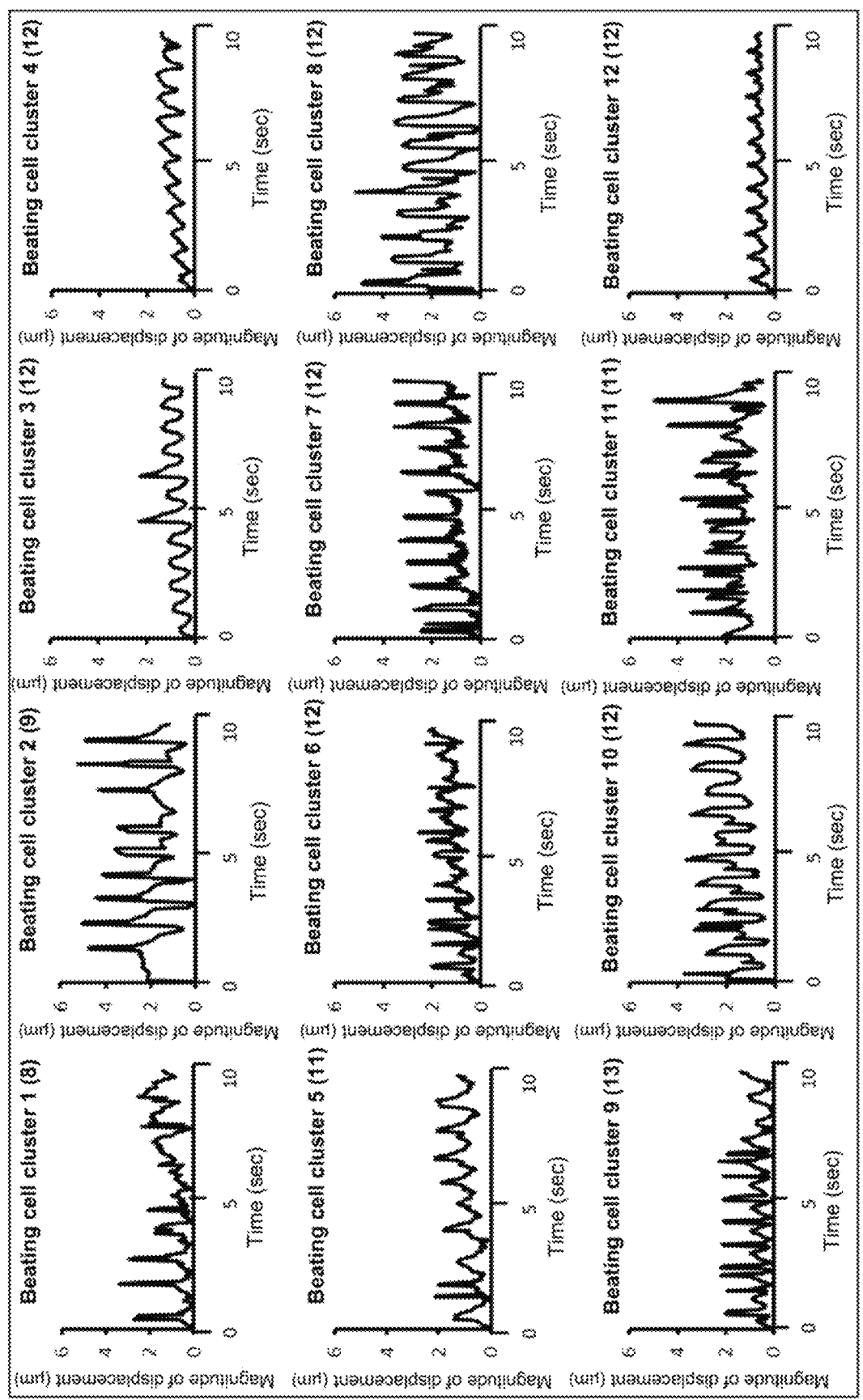
FIG. 3 graphically illustrates the number of beats and the magnitude of displacement of each of 12 beating cell clusters of FIG. 1B in 10 seconds.

The results of the observation of the beating behavior of the cells obtained by induced differentiation of the hiPS cells (253G1 cell line) into cardiomyocytes are shown in FIGS. 1, 2 and 3. FIGS. 1A and 1B are still frames from separate 10-second movies of beating cell cluster(s). FIG. 1A shows the results for the cells obtained by induced differentiation on the LN511E8-coated plate. FIG. 1B shows the results for the cells obtained by induced differentiation on the P-511E8 (D1; a-C)-coated plate. The area encircled by a dashed line represents one beating cell cluster. On the LN511E8-coated plate, one beating cell cluster was observed in one field of view. In contrast, on the P-511E8(D1; a-C)-coated plate, 12 beating cell clusters were observed in one field of view.

FIG. 2 graphically illustrates the number of beats and the magnitude of displacement of the beating cell cluster of FIG. 1A in 10 seconds. FIG. 3 graphically illustrates the number of beats and the magnitude of displacement of each of the 12 beating cell clusters of FIG. 1B in 10 seconds. In the graphs of FIGS. 2 and 3, the X-axis represents the time in seconds, and the Y-axis represents the magnitude (unit: μm) of displacement from the original position (selected spot) due to beating. The beating cell cluster on the LN511E8-coated plate beat 5 times in 10 seconds, whereas the individual beating cell clusters on the P-511E8 (D1; a-C)-coated plate beat 8 to 13 times in 10 seconds, showing a beating behavior more similar to those of human cardiomyocytes.

(2) FACS Analysis (2-1) Results for Differentiated Cells from hiPS Cells (253G1 Cell Line)

Figure 4:
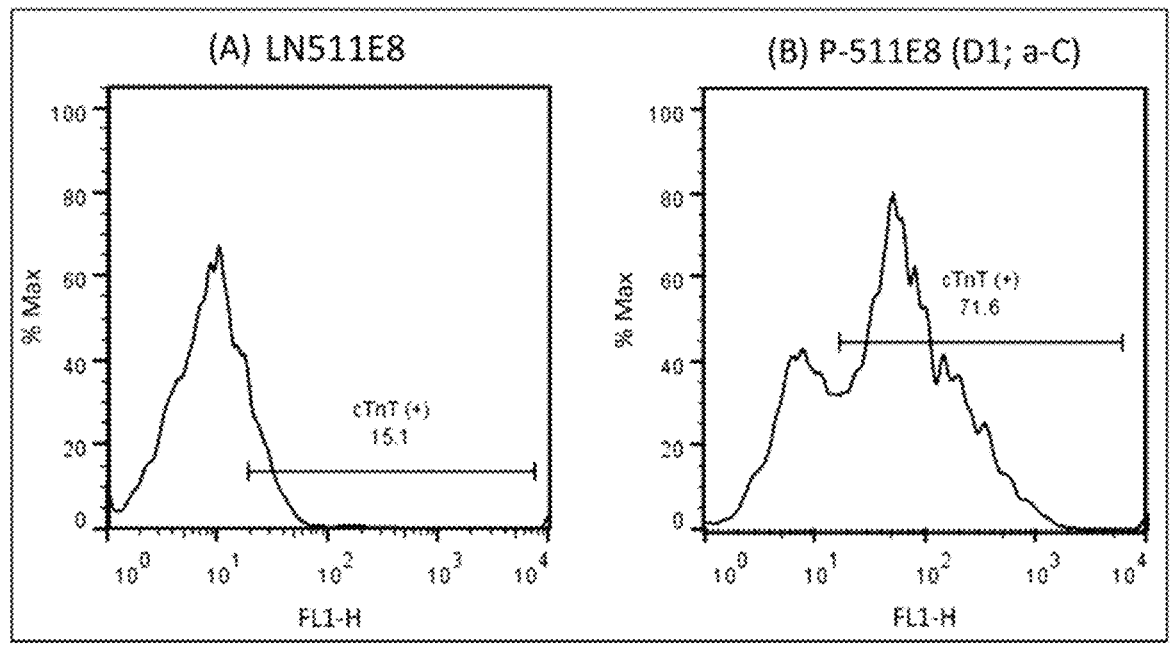
FIGS. 4A and 4B show the results of FACS analysis for troponin T (cTnT)-positive cells in the cells obtained by induced differentiation of human iPS cells (253G1 cell line) into cardiomyocytes.

The results are shown in FIG. 4. FIG. 4A shows the results for the LN511E8-coated plate, and FIG. 4B shows the results for the P-511E8 (D1; a-C)-coated plate. The fraction of cTnT-positive cells in FIG. 4A was 15.1%. In contrast, the fraction of cTnT-positive cells in FIG. 4B was 71.6%.

(2-2) Results for differentiated cells from hiPS cells (201B7 cell line)

Figure 5:
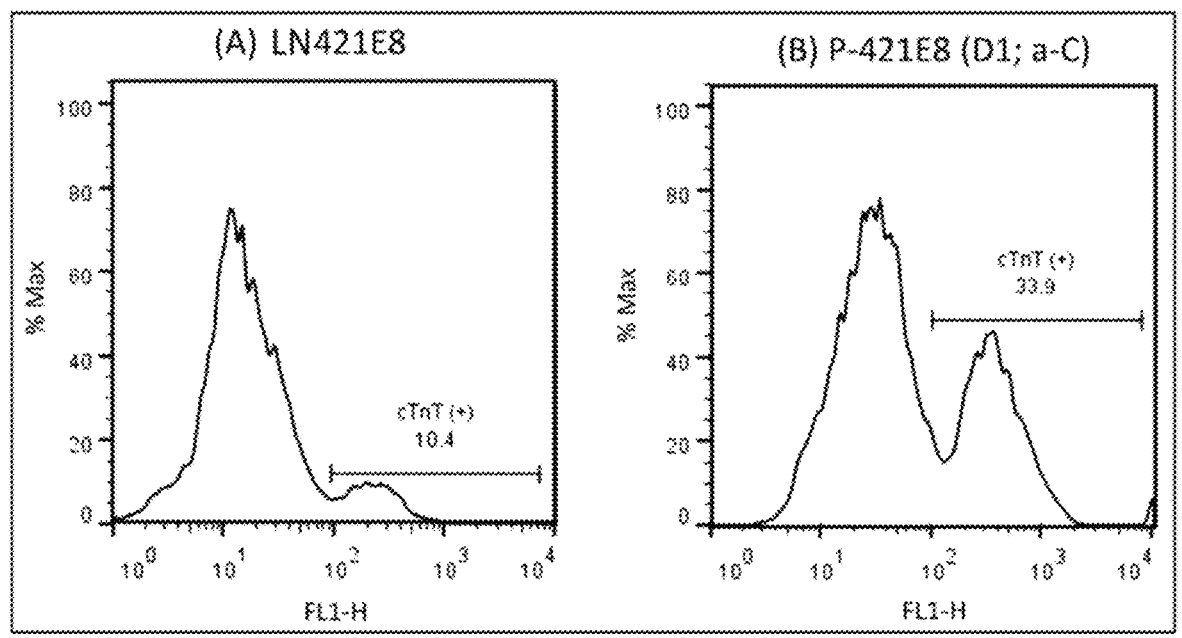
FIGS. 5A and 5B show the results of FACS analysis for troponin T (cTnT)-positive cells in the cells obtained by induced differentiation of human iPS cells (201B7 cell line) into cardiomyocytes.

The results are shown in FIG. 5. FIG. 5A shows the results for the LN421E8-coated plate, and FIG. 5B shows the results for the P-421E8(D1; a-C)-coated plate. The fraction of cTnT-positive cells in FIG. 5A was 10.4%. In contrast, the fraction of cTnT-positive cells in FIG. 5B was 33.9%.

The above results show the usefulness and advantage of using P-511E8(D1; a-C)- or P-421E8(D1; a-C)-coated plates in induced differentiation of hiPS cells into cardiomyocytes.

Example 2

Examination of the Usefulness of a Conjugate of Laminin E8 and Perlecan Domain 1 in Induced Differentiation of Human iPS Cells into Skeletal Muscle Cells (1) Experimental Materials and Methods (1) Laminin E8 and Conjugates of Laminin E8 and Perlecan Domain 1

LN421E8, P-421E8(D1; a-C) and P-511E8(D1; a-C) were used. These were all the same as those used in Example 1.

(2) hiPS Cells hiPS cell line 201B7 was used. The 201B7 cell line was engineered to contain a tdTomato sequence at the 5' end of the initiation codon of the MYF5 locus in the usual manner of homologous recombination using the CRISPR/CAS9 system. Thus, an iPS cell line expressing tdTomato in coordination with the expression of MYF5 (MYF5-tdTomato C3 iPSC, hereinafter referred to as "MYF5-tdTomato") was prepared. MYF5-tdTomato was confirmed to have a single genetically modified allele.

(3) Pre-Culture of hiPS Cells

The culture medium in each well of a 6-well plate in which the hiPS cells were maintained was aspirated off. The cells in each well were washed with 1 mL of PBS(−) and incubated with 500 μL of Accutase at 37° C. for 10 minutes. The cells were detached by pipetting, and after addition of 2 mL of StemFit AK02N medium (Ajinomoto), harvested into a tube. After centrifugation at 900 rpm for 5 minutes, the supernatant was removed. The cells were resuspended in 1 to 2 mL of StemFit AK02N medium supplemented with 10 μM Y-27632 and then counted.

Six-well culture plates were coated by adding 1.5 mL/well of a coating solution containing 22 nM P-511E8 (D1; a-C), 22 nM P-421E8(D1; a-C), or 22 nM LN421E8, and the plates were allowed to stand at 37° C. for 1 hour. Another plate was coated by adding Matrigel diluted 100-fold with a hiPS cell maintenance medium (KSR medium without bFGF) to each well, and the plate was allowed to stand at 37° C. overnight. The coating solution in each well was aspirated off, the hiPS cells (MYF5-tdTomato or 201B7) dissociated as single cells were seeded at $1 \times 10^4$ cells/well, and pre-culture was started (Day-3). On the following day (Day −2), the culture medium was replaced with StemFit AK02N supplemented with 10 μM Y-27632, and the culture was continued for 2 days.

(4) Induced Differentiation into Skeletal Muscle Cells

On the initial day of induced differentiation (Day 0), the culture medium was replaced with differentiation medium A (2 mL/well). The differentiation medium A was CDMi basal medium (a 1:1 mixture of Iscove's Modified Dulbecco's Medium (Ser. No. 12/440,053, Invitrogen) and Ham's F-12 Nutrient Mixture (Ser. No. 11/765,054, Invitrogen) supplemented with 1% Penicillin-Streptomycin Mixed Solution (Nacalai Tesque), 1% CD Lipid Concentrate (Invitrogen), 1% Insulin-Transferrin-Selenium (Invitrogen) and 450 μM 1-thioglycerol (SIGMA)) supplemented with 5 μM SB431542 and 10 μM CHIR99021. Afterwards, medium replacement was performed on the 2nd day (Day 2) and the 5th day (Day 5).

On the 7th day (Day 7), the cells were passaged in the following manner. The culture medium was aspirated off, and the cells were washed twice with PBS(−). The cells were incubated with 500 μL of 0.25% Trypsin/1 mM EDTA at 37° C. for 5 minutes. After addition of 2.5 mL of CDMi basal medium, the cells were dissociated into single cells by pipetting. After centrifugation at 900 rpm at 4° C. for 5 minutes, the supernatant was removed. The cells were resuspended in CDMi basal medium and then counted. The differentiation medium A (2 mL/well) was added to 6-well culture plates coated with Matrigel, LN421E8, P-421E8(D1; a-C) or P-511E8(D1; a-C), which were prepared on the previous day, and the cells were seeded thereon at $4 \times 10^5$ cells/well. Medium replacement was performed on the 8th day (Day 8), the 10th day (Day 10) and the 12th day (Day 12).

On the 14th day (Day 14), the cells were passaged in the same manner as on Day 7 except that the culture medium was changed to CDMi basal medium supplemented with 10 μM Y-27632. The seeding cell number was $6 \times 10^3$ cells/dish for a 10-cm dish, $2 \times 10^3$ cells/dish for a 6-cm dish, and $1 \times 10^3$ cells/well for a 6-well plate.

On the 17th day (Day 17), the culture medium was changed to a muscle differentiation medium. The muscle differentiation medium was S-Clone SF-03 (ss1303, Sanko Junyaku) supplemented with 0.2% BSA, 200 μM 2-ME, 10 ng/mL IGF-1 (PeproTech), 10 ng/mL HGF (PeproTech) and 10 ng/mL bFGF (Oriental Yeast). Medium replacement was performed using a fresh muscle differentiation medium twice a week until the 38th day.

In the case where the culture was continued after the 38th day (Day 38), the medium was changed to a maturation medium on Day 38, and afterwards, medium replacement was performed 3 times a week during the culture. The maturation medium was DMEM basal medium (DMEM medium with 0.5% Penicillin-Streptomycin Mixed Solution (Nacalai Tesque), 1 mM L-glutamine (Nacalai Tesque) and 50 μM 2-ME) supplemented with 2% horse serum (HS), 5 μM SB431542 and 10 ng/mL IGF-1.

(5) Immunostaining

The cells attached on the plate on the 38th day of induced differentiation were directly fixed with a 2% paraformaldehyde solution in PBS(−) at 4° C. for 10 minutes. After removal of the paraformaldehyde, the attached cells were washed 3 times with PBS(−) and then blocked in Blocking One (Nacalai Tesque) at room temperature for 1 hour. As primary antibodies, a mouse anti-myosin heavy chain (MHC) antibody (eBioscience) and a rabbit anti-MyoD antibody (Abcam) were separately diluted 400-fold with Blocking One diluted 10-fold with 0.1% Triton-X 100/PBS (−), and then added to the attached cells from which the Blocking One was removed beforehand. Incubation was performed at room temperature for 60 minutes. After 3 times of washing with 0.1% Triton-X 100/PBS(−), an Alexa Fluor 488-labeled anti-rabbit IgG antibody and an Alexa Fluor 568-labeled anti-mouse IgG antibody, which were separately diluted 500-fold with Blocking One diluted 10-fold with 0.1% Triton-X 100/PBS(−), were added, followed by incubation in a light-shielding condition at room temperature for 60 minutes. After 3 times of washing with 0.1% Triton-X 100/PBS(−), the cells were counterstained with DAPI (Thermo Fisher) diluted 50,000-fold with PBS(−) in a light-shielding condition at room temperature for 5 minutes. After 3 times of washing with PBS(−), MHC- and MyoD-positive cells were observed with the BZ-X700 all-in-one fluorescence microscope.

(6) Quantification of gene expression levels

The cells on the 14th day of differentiation were harvested, and the gene expression levels of SIX1 and Sox1 were quantified. In addition, the cells on the 38th day of differentiation were harvested, and the gene expression levels of MyoD, myosin heavy chain (MHC), myogenin and Pax7 were quantified. The specific procedure was as follows. RNA was purified from the harvested cells using ReliaPrep RNA Cell Miniprep System (Promega). From 1 μg of the purified RNA, cDNA was synthesized with a ReverTra Ace-α-kit (Toyobo). The genes of interest were amplified by quantitative PCR from the obtained cDNA as a template using Power SYBR Green Master Mix (Thermo Fisher) and the specific primers for each gene. PCR reaction and analysis were performed with the StepOnePlus Real-Time PCR System (Thermo Fisher) according to the standard protocol. Separately, undifferentiated hiPS cells were transplanted into immunodeficient mice to form teratomas, RNA was purified from the teratomas, and cDNA was synthesized and used as a positive control template for standard curve preparation. The relative expression level of each gene in the differentiated cells was calculated on the assumption that the corresponding expression level in the teratomas was 1. The amount of total RNA was normalized to the expression level of the endogenous control β actin.

(7) FACS Analysis

The cells on the 18th and 85th days of differentiation were treated with 0.2% collagenase I (Sigma) at 37° C. for 30 minutes. The cells were detached from the dish and further treated with Accutase (Nacalai Tesque) at 37° C. for 10 minutes. The cells were dissociated into single cells by repeated pipetting. After centrifugation, the supernatant was removed, and the cell pellet was suspended in 1 mL of HBSS(−) (Thermo Fisher) supplemented with 1% BSA. The expression level of tdTomato was determined using the LSRFortessa cell analyzer (BD Biosciences).

Results 1:

Evaluation of Induced Differentiation of MYF5-tdTomato into Skeletal Muscle Cells The hiPS cell line MYF5-tdTomato was subjected to induced differentiation into skeletal muscle cells on Matrigel-, LN421E8-, P-421E8(D1; a-C)- or P-511E8(D1; a-C)-coated plates in the above-described manner. The expression levels of the SIX1 gene (expressed in the skeletal muscle) and the Sox1 gene (expressed in the nerve) in the cells on the 14th day were quantified. The fraction of cells positive for Myf5 (skeletal muscle stem cell marker) in the cells on the 18th and 85th days was determined by FACS analysis. The expression of MHC and MyoD in the cells on the 38th day was examined by immunostaining.

(1) Immunostaining

Figure 6:
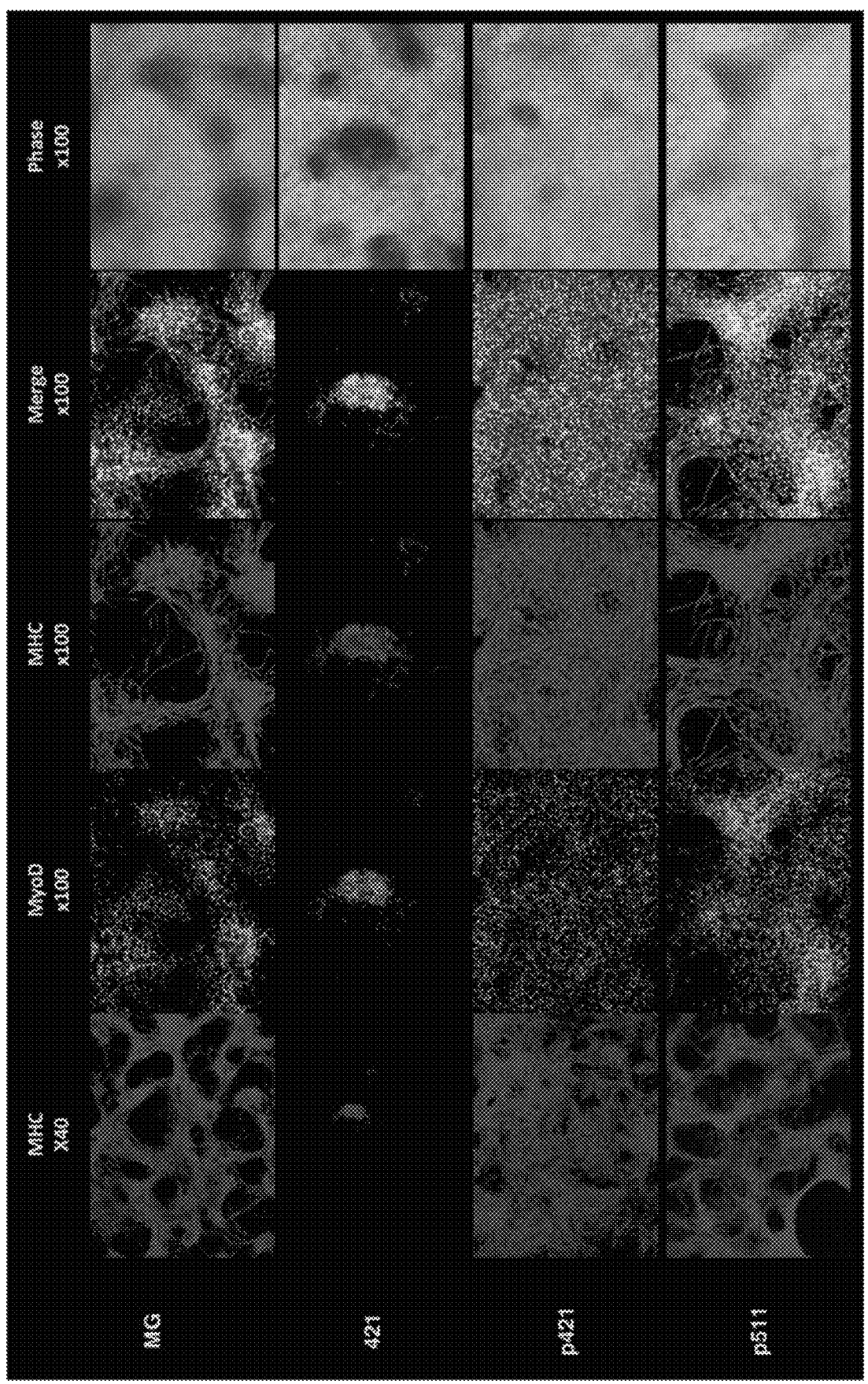
FIG. 6 shows the expression of myosin heavy chain (MHC) and MyoD examined by immunostaining in the cells on the 38th day of induced differentiation into skeletal muscle cells from human iPS cells expressing tdTomato in coordination with the expression of MYF5 (MYF5-tdTomato). The top row shows the results for the cells on a plate coated with Matrigel. The 2nd row shows the results for the cells on a plate coated with a human laminin α4β2γ1 E8 fragment. The 3rd row shows the results for the cells on a plate coated with a conjugate in which human perlecan domain 1 is fused to the α4 chain C-terminus of a human laminin α4β2γ1 E8 fragment. The bottom row shows the results for the cells on a plate coated with a conjugate in which human perlecan domain 1 is fused to the α5 chain C-terminus of a human laminin α5β1γ1 E8 fragment.

The expression of MHC and MyoD examined by immunostaining in the cells on the 38th day are shown in FIG. 6. On the Matrigel-coated plate (top row: MG), the area containing MHC-positive cells and/or MyoD-positive cells and the area (black area) not containing the positive cells were observed in the field of view. On the LN421E8-coated plate (2nd row: 421), MHC-positive cells and MyoD-positive cells were present in only part of the field of view, indicating that differentiation efficiency was lower than that on the Matrigel-coated plate. In contrast, on the P-421E8 (D1; a-C)-coated plate (3rd row: p421), MHC-positive cells and MyoD-positive cells were observed in the entire field of view, indicating that differentiation efficiency was markedly higher than that on the Matrigel-coated plate. On the P-511E8 (D1; a-C)-coated plate (bottom row: p511), both the area containing MHC-positive cells and/or MyoD-positive cells and the area (black area) not containing the positive cells were observed in the field of view as was the case on the Matrigel-coated plate, but the positive cell-containing area was larger than that on the Matrigel-coated plate.

(2) Gene expression

Figure 7:
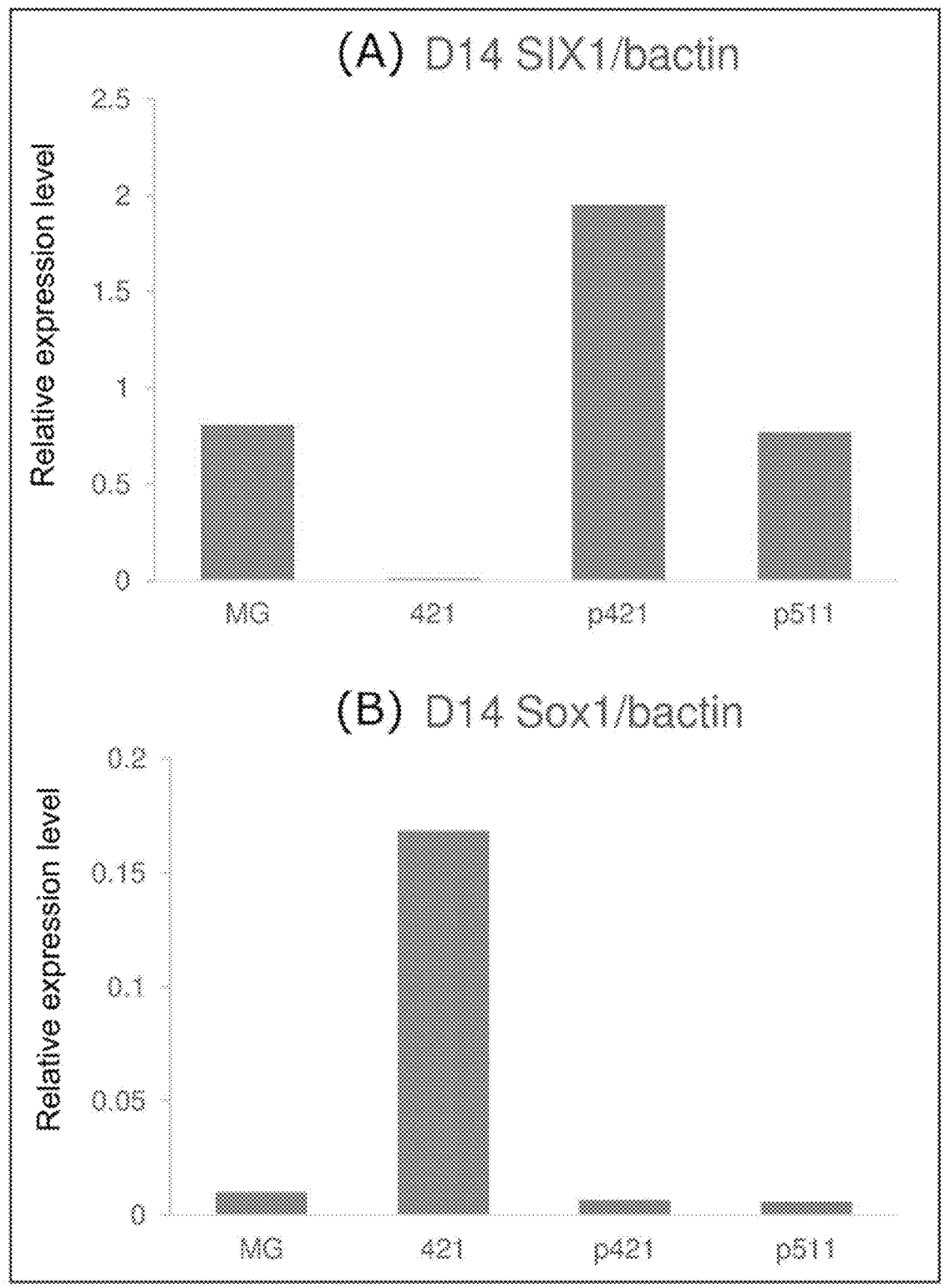
FIGS. 7A and 7B show the quantified expression levels of the SIX1 and Sox1 genes in the cells on the 14th day of induced differentiation into skeletal muscle cells from human iPS cells expressing tdTomato in coordination with the expression of MYF5 (MYF5-tdTomato).

The quantified expression levels of the SIX1 and Sox1 genes in the cells on the 14th day are shown in FIG. 7. FIG. 7A shows the results for the SIX1 gene, and FIG. 7B shows the results for the Sox1 gene. The expression level of the SIX1 gene, which is expressed in the skeletal muscle, was 2 or more times higher in the cells on the P-421E8 (D1; a-C)-coated plate ("p421" in the figure) than that in the cells on the Matrigel-coated plate ("MG" in the figure). In the cells on the P-511E8(D1; a-C)-coated plate ("p511" in the figure), the SIX1 gene expression level was comparable to that in the cells on the Matrigel-coated plate. In the cells on the LN421E8-coated plate ("421" in the figure), the SIX1 gene was hardly expressed. The expression level of the Sox1 gene, which is expressed in the nerve, was high in the cells on the LN421E8-coated plate ("421" in the figure), but in the cells on the other plates, the Sox1 gene was hardly expressed.

(3) FACS Analysis

Figure 8:
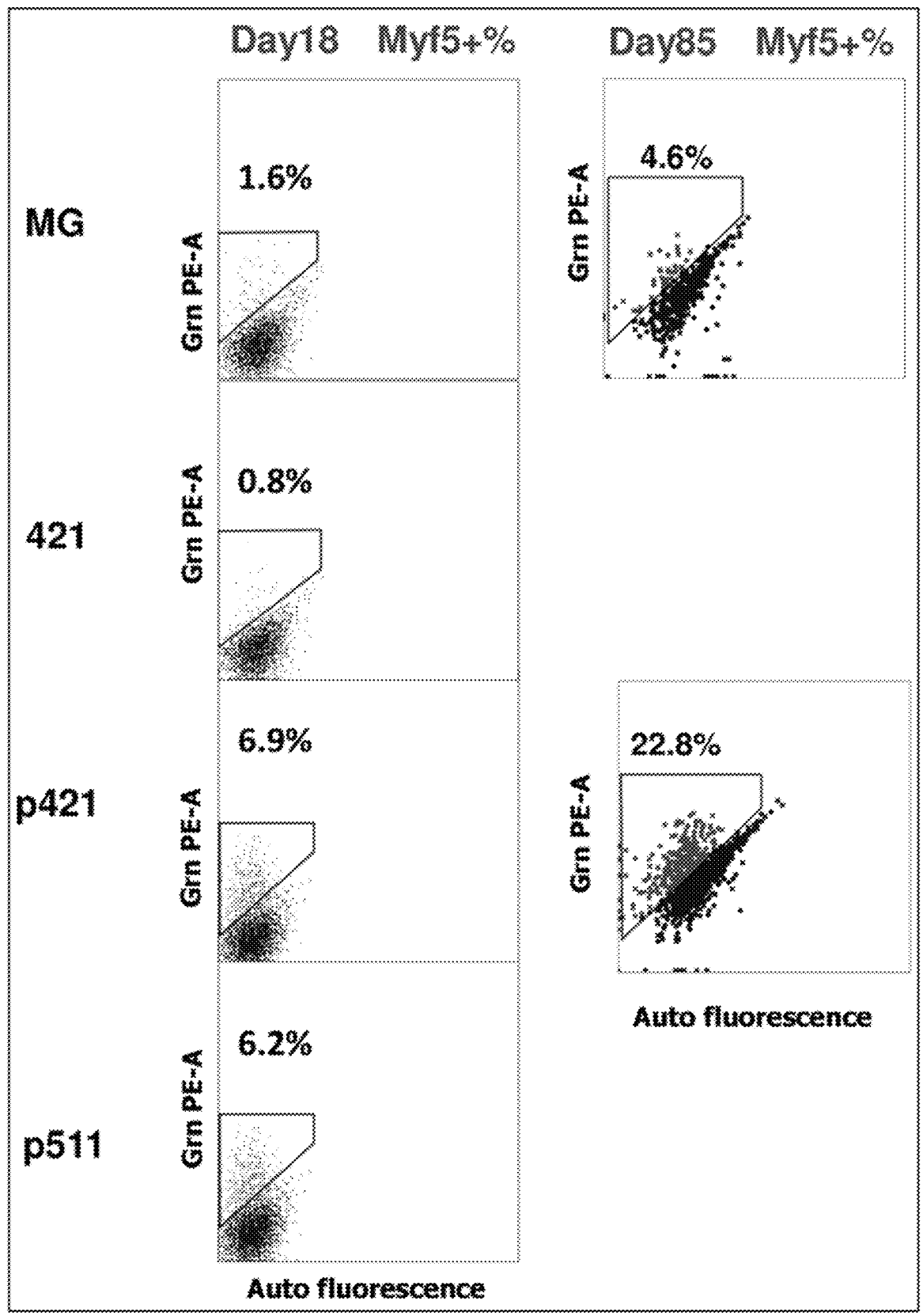
FIG. 8 shows the fraction of Myf5-positive cells determined by FACS analysis of the cells obtained by induced differentiation into skeletal muscle cells from human iPS cells expressing tdTomato in coordination with the expression of MYF5 (MYF5-tdTomato). The left column shows the results for the cells on the 18th day, and the right column shows the results for the cells on the 85th day.

The fraction of cells positive for Myf5 (skeletal muscle stem cell marker) determined by FACS analysis of the cells on the 18th and 85th days was shown in FIG. 8. The left column shows the results for the cells on the 18th day, and the right column shows the results for the cells on the 85th day. As of the 18th day, the fraction of Myf5-positive cells was 6.9% of the cells on the P-421E8(D1; a-C)-coated plate ("p421" in the figure), which was markedly higher than that on the Matrigel-coated plate ("MG" in the figure) 1.6%). On the 85th day, the fraction of Myf5-positive cells was 4.6% on the Matrigel-coated plate, but was 22.8% on the P-421E8 (D1; a-C)-coated plate.

Results 2:

Evaluation of Induced Differentiation of 201B7 Cell Line into Skeletal Muscle Cells The hiPS cell line 201B7, which is known to be stable in an undifferentiated state and less susceptible to differentiation, was subjected to induced differentiation into skeletal muscle cells on Matrigel- or P-421E8 (D1; a-C)-coated plates in the above-described manner. The expression of MHC and MyoD in the cells on the 38th day was examined by immunostaining. In addition, the expression levels of skeletal muscle marker genes (MyoD, MHC, myogenin and Pax7) in the cells on the 38th day were quantified.

Figure 9:
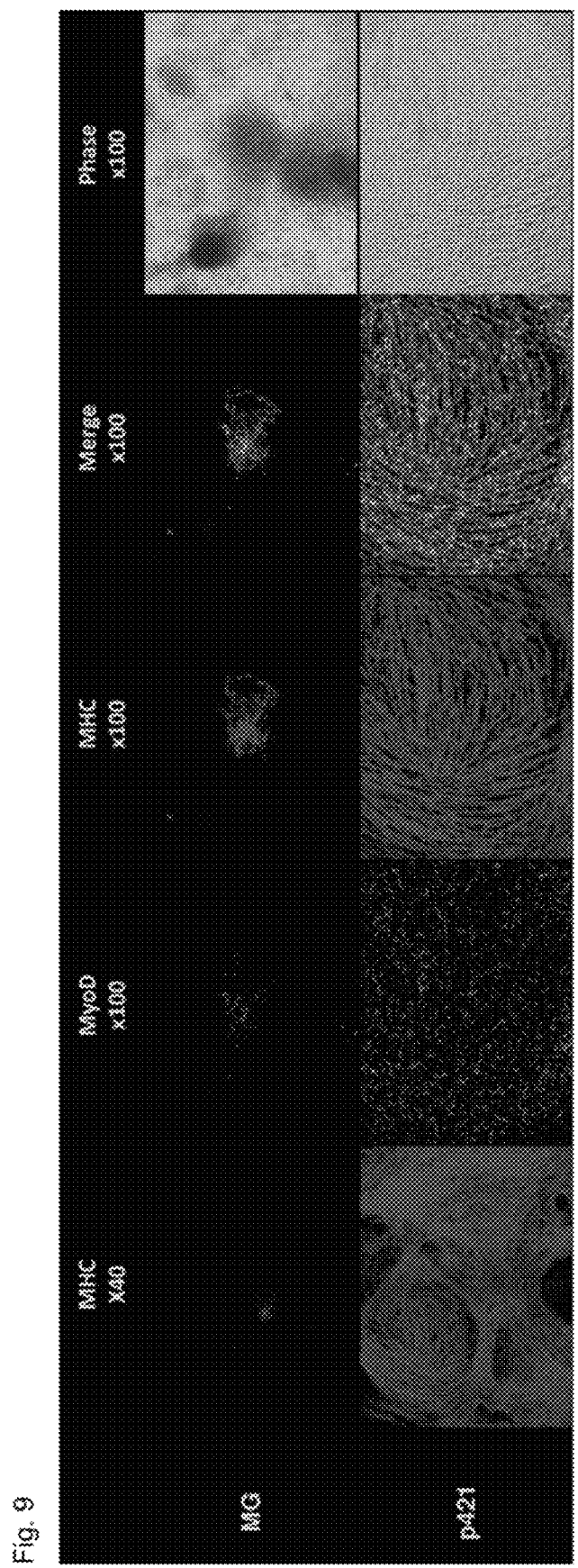
FIG. 9 shows the expression of myosin heavy chain (MHC) and MyoD examined by immunostaining in the cells on the 38th day of induced differentiation of human iPS cells (201B7 cell line) into skeletal muscle cells. The top row shows the results for the cells on a plate coated with Matrigel. The bottom row shows the results for the cells on a plate coated with a conjugate in which human perlecan domain 1 is fused to the α4 chain C-terminus of a human laminin α4β2γ1 E8 fragment.

The expression of MHC and MyoD examined by immunostaining in the cells on the 38th day are shown in FIG. 9. On the Matrigel-coated plate (top row: MG), MHC-positive cells and MyoD-positive cells were observed in part of the field of view, and differentiation efficiency was low. In contrast, on the P-421E8 (D1; a-C)-coated plate (bottom row: p421), MHC-positive cells and MyoD-positive cells were observed in the entire field of view, indicating that differentiation efficiency was markedly high.

Figure 10:
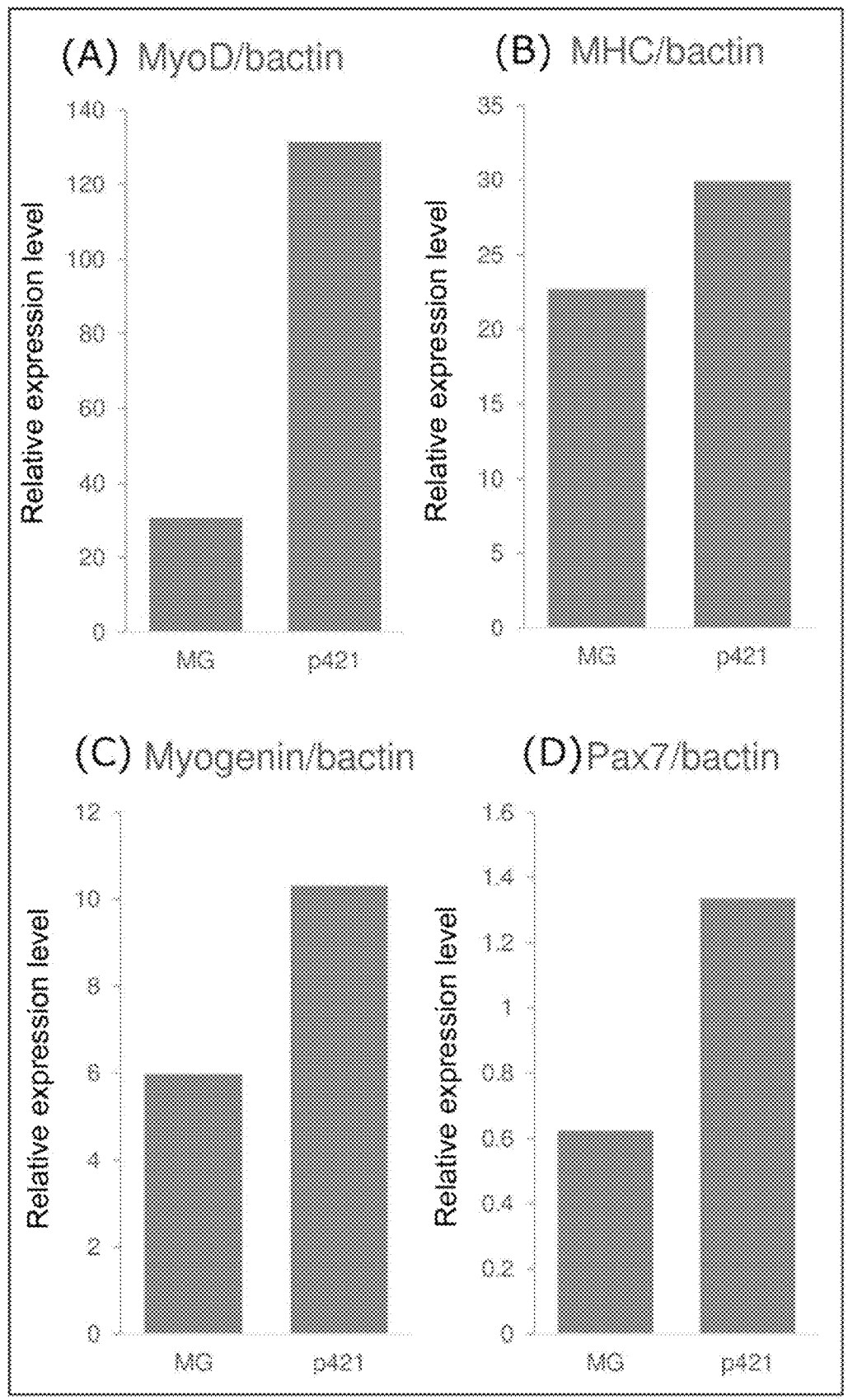
FIGS. 10A to 10D show the quantified expression levels of skeletal muscle marker genes (MyoD, myosin heavy chain (MHC), myogenin and Pax7) in the cells on the 38th day of induced differentiation of human iPS cells (201B7 cell line) into skeletal muscle cells.

The quantified expression levels of the skeletal muscle marker genes (MyoD, MHC, myogenin and Pax7) in the cells on the 38th day are shown in FIG. 10. FIG. 10A shows the results for the MyoD gene, FIG. 10B shows the results for the MHC gene, FIG. 10C shows the results for the myogenin gene, and FIG. 10D shows the results for the Pax7 gene. The expression levels of these genes were all higher in the cells on the P-421E8 (D1; a-C)-coated plate than those in the cells on the Matrigel-coated plate.

The above results show the usefulness and advantage of using P-421E8 (D1; a-C)-coated plates in induced differentiation of hiPS cells into skeletal muscle cells. Also shown is that the differentiation efficiency on P-511E8 (D1; a-C)-coated plates was comparable to that on Matrigel-coated plates.

Example 3

Examination of the Usefulness of a Conjugate of Laminin E8 and Perlecan Domain 1 in Induced Differentiation of Human iPS Cells into Skeletal Muscle Cells (2)
Experimental Materials and Methods
(1) Laminin E8s and Conjugates of Laminin E8 and Perlecan Domain 1

In addition to LN421E8, P-421E8 (D1; a-C) and P-511E8 (D1; a-C), which were used in Example 2, human laminin 111E8 (hereinafter referred to as "LN111E8") and a conjugate in which human perlecan domain 1 was fused to the α1 chain C-terminus of LN111E8 (hereinafter referred to as "P-111E8 (D1; a-C)"); human laminin 211E8 (hereinafter referred to as "LN211E8") and a conjugate in which human perlecan domain 1 was fused to the α2 chain C-terminus of LN211E8 (hereinafter referred to as "P-211E8 (D1; a-C)"); human laminin 332E8 (hereinafter referred to as "LN332E8") and a conjugate in which human perlecan domain 1 was fused to the α3 chain C-terminus of LN332E8 (hereinafter referred to as "P-332E8 (D1; a-C)"); human laminin 411E8 (hereinafter referred to as "LN411E8") and a conjugate in which human perlecan domain 1 was fused to the α4 chain C-terminus of LN411E8 (hereinafter referred to as "P-411E8 (D1; a-C)"); human laminin 511E8 (hereinafter referred to as "LN511E8"); and human laminin 521E8 (hereinafter referred to as "LN521E8") and a conjugate in which human perlecan domain 1 was fused to the α5 chain C-terminus of LN521E8 (hereinafter referred to as "P-521E8(D1; a-C)") were used. Each laminin E8 was prepared according to an appropriately modified version of the method of Ido et al. (Hiroyuki Ido et al., J. Biol. Chem., 282, 11144-11154, 2007). Each conjugate in which a different laminin E8 and perlecan domain 1 were fused was prepared according to an appropriately modified version of the method of WO 2014/199754 A1.

Figure 11:
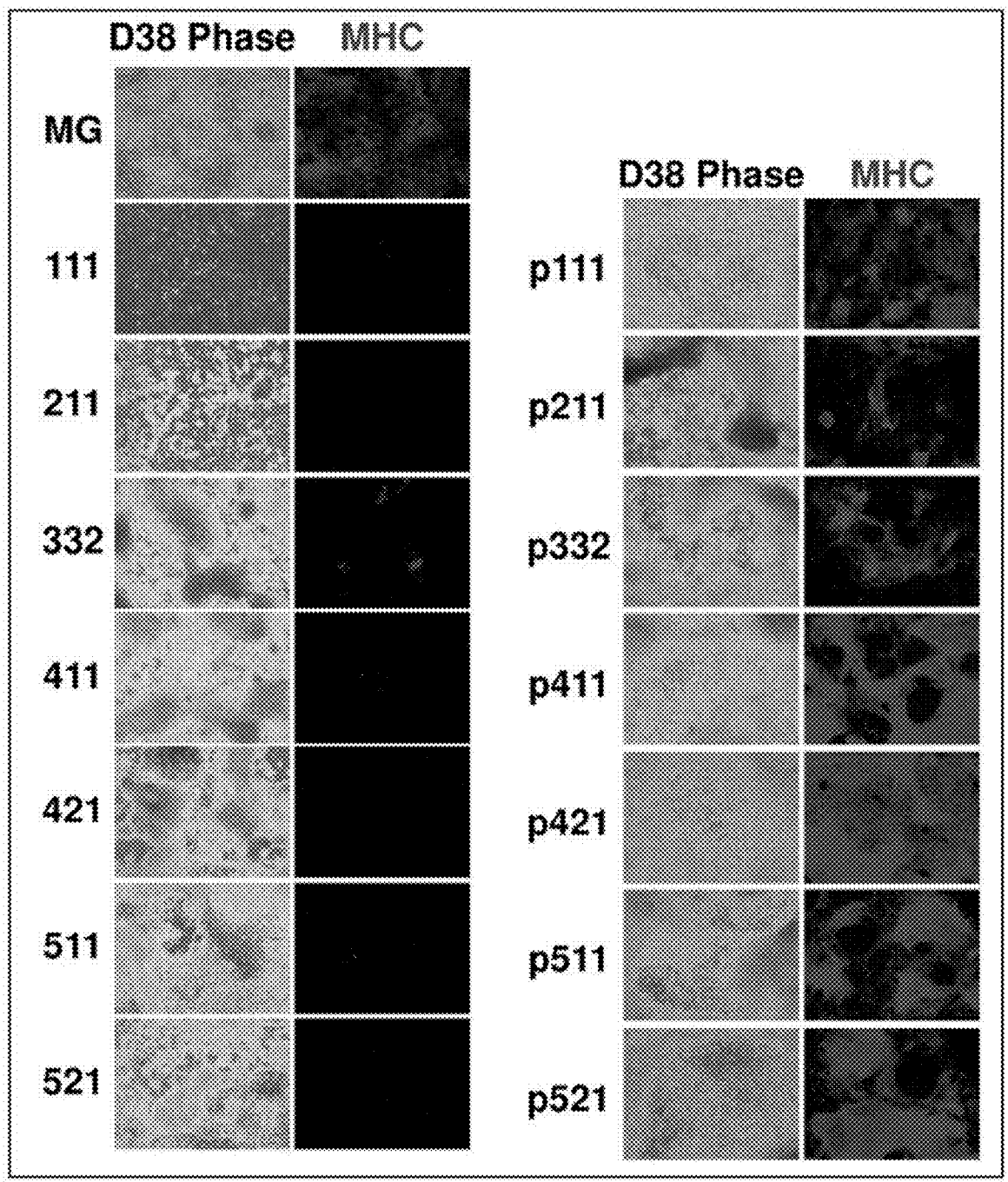
FIG. 11 shows the expression of myosin heavy chain (MHC) examined by immunostaining in the cells on the 38th day of induced differentiation of human iPS cells (201B7 cell line) into skeletal muscle cells. The 1st row on the left shows the results for the cells on a plate coated with Matrigel. The 2nd to 8th rows on the left show the results for the cells on plates coated with different human laminin E8 fragments. The 1st to 7th rows on the right show the results for the cells on plates coated with different conjugates in each of which human perlecan domain 1 is fused to the α chain C-terminus of a different human laminin E8 fragment.

(2) hiPS Cells
hiPS cell line 201B7 was used.
(3) Pre-Culture of hiPS Cells
Pre-culture was performed in the same manner as in Example 2 (3) using plates coated with the above laminin E8s, the above conjugates and Matrigel.
(4) Induced Differentiation into Skeletal Muscle Cells
Induced differentiation into skeletal muscle cells was performed in the same manner as in Example 2 (4) using plates coated with the above laminin E8s, the above conjugates and Matrigel.
(5) Immunostaining
Immunostaining was performed in the same manner as in Example 2 (5) except for not using the rabbit anti-MyoD antibody (Abcam) or the Alexa Fluor 488-labeled anti-rabbit IgG antibody.
(6) Quantification of Gene Expression Levels
The cells on the 14th day of differentiation were harvested, and the gene expression levels of the dermomyotome markers SIX1 and DMRT2 were quantified. The quantification of the gene expression levels was performed in the same manner as in Example (6).
Results
(1) Immunostaining The expression of MHC examined by immunostaining in the cells on the 38th day of induced differentiation is shown in FIG. 11. On the Matrigel-coated plate (1st row on the left: MG), the area containing MHC-positive cells and the area (black area) containing no MHC-positive cells were observed in the field of view. On each plate coated with a different laminin E8 (2nd to 8th rows on the left: 111 to 521), MHC-positive cells were hardly present. In contrast, on each plate coated with a different conjugate (1st to 7th rows on the right: p111 to p521), MHC-positive cells were present. In particular, on the P-421E8(D1; a-C)-coated plate (5th row on the right: p421), MHC-positive cells were observed in the entire field of view, similarly to the results of Example 2, indicating that differentiation efficiency was markedly higher than that on the Matrigel-coated plate. On the P-411E8(D1; a-C)-coated plate, the P-511E8(D1; a-C)-coated plate, and the P-521E8(D1; a-C)-coated plate (4th, 6th and 7th rows on the right: p411, p511 and p521), the area containing MHC-positive cells was comparable in size to that on the Matrigel-coated plate (1st row on the left: MG). In contrast, on the P-111E8(D1; a-C)-coated plate, the P-211E8(D1; a-C)-coated plate and the P-3321E8(D1; a-C)-coated plate (1st to 3rd rows on the right: p111, p211, p322), the area containing MHC-positive cells was smaller than that on the Matrigel-coated plate.

(2) Gene Expression

Figure 12:
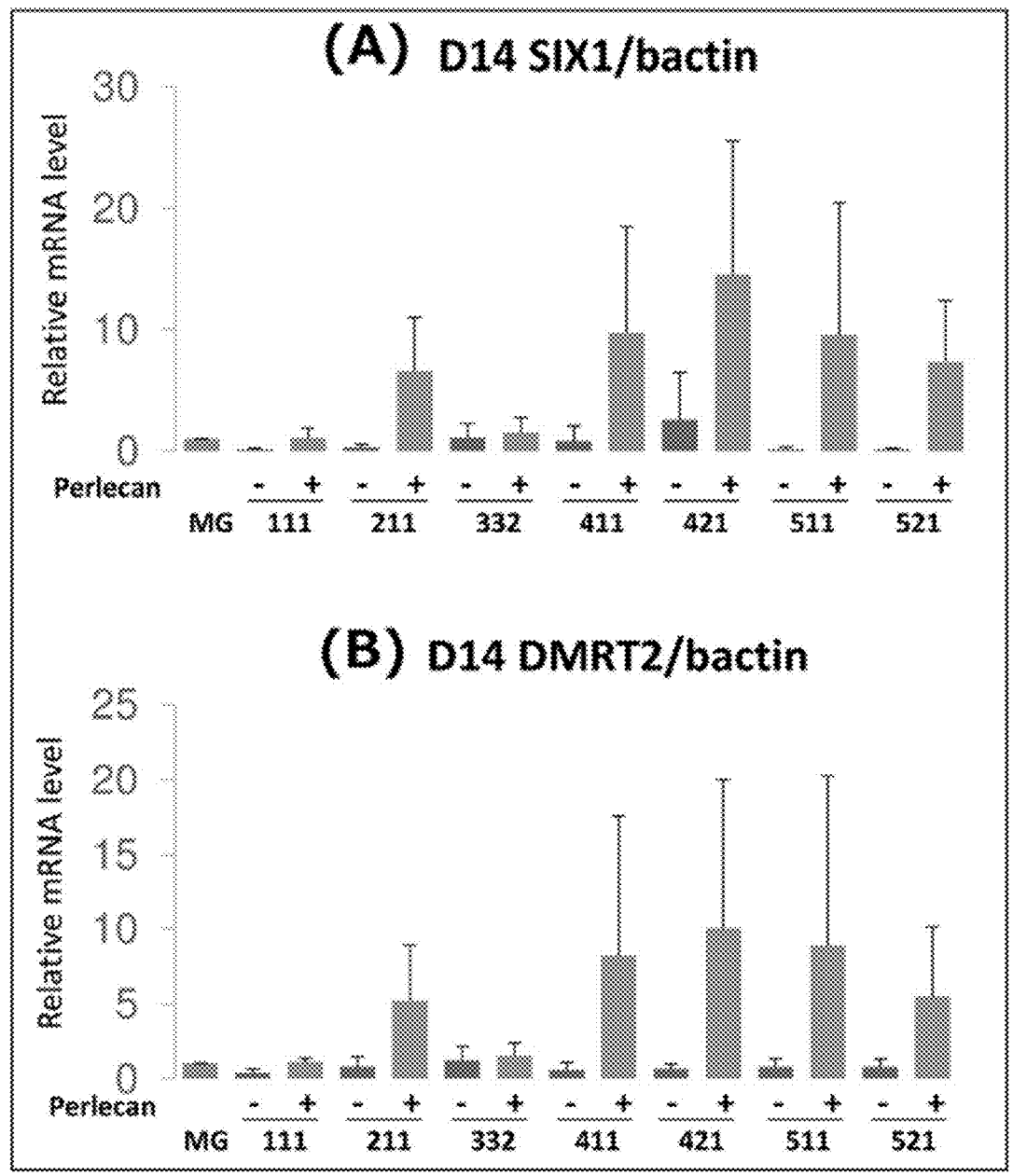
FIGS. 12A and 12B show the quantified expression levels of the SIX1 and DMRT2 genes in the cells on the 14th day of induced differentiation of human iPS cells (201B7 cell line) into skeletal muscle cells.

The quantified expression levels of the SIX1 and DMRT2 genes in the cells on the 14th day are shown in FIG. 12. FIG. 12A shows the results for the SIX1 gene, and FIG. 12B shows the results for the DMRT2 gene. The expression levels of the both genes in the cells on each plate coated with a different laminin E8 ("Perlecan −" in the figure), the P-111E8(D1; a-C)-coated plate ("111+" in the figure) and the P-332E8(D1; a-C)-coated plate ("332+" in the figure) were comparable to those in the cells on the Matrigel-coated plate. In contrast, the expression levels of the both genes in the cells on the P-211E8(D1; a-C)-coated plate ("211+" in the figure), the P-411E8(D1; a-C)-coated plate ("411+" in the figure), the P-421E8(D1; a-C)-coated plate ("421+" in the figure), the P-511E8(D1; a-C)-coated plate ("511+" in the figure) and the P-521E8(D1; a-C)-coated plate ("521+" in the figure) were markedly higher than those in the cells on the Matrigel-coated plate. In particular, the expression levels in the cells on the P-421E8(D1; a-C)-coated plate were the highest.

(3) Summary

The above results show the usefulness and advantage of using P-421E8(D1; a-C)-coated plates in induced differentiation of hiPS cells into skeletal muscle cells. Also shown is that the differentiation efficiency on P-411E8(D1; a-C)-, P-511E8(D1; a-C)- or P-521E8(D1; a-C)-coated plates was comparable to that on Matrigel-coated plates.

Example 4

Examination of the Efficacy of a Conjugate of Laminin E8 and a Heparan Sulfate Chain-Lacking Form of Perlecan Domain 1 in Induced Differentiation of Human iPS Cells into Skeletal Muscle Cells Experimental Materials and Methods (1) Laminin E8 and Conjugate of Laminin E8 and Perlecan Domain 1

LN421E8 and P-421E8(D1; a-C) were used.

(2) hiPS Cells hiPS cell line 201B7 was used.

(3) Plate Coating

Six-well culture plates were coated by adding 1.5 mL/well of a coating solution containing 22 nM P-421E8 (D1; a-C) or 22 nM LN421E8, and the plates were allowed to stand at 4° C. overnight.

(4) Heparitinase Treatment of P-421E8(D1; a-C)-Coated Plate

A coating solution containing 22 nM P-421E8(D1; a-C) was added to a plate in a volume of 1.5 mL/well, and the plate was allowed to stand at 4° C. overnight. The plate was washed 3 times with Tris-buffered saline (TBS) supplemented with 0.1% recombinant human serum albumin (rHSA). TBS supplemented with 1% skim milk was added, and the plate was allowed to stand at room temperature for 1 hour for blocking. After 3 times of washing with 0.1% rHSA/TBS, 1.5 mL of a heparitinase solution (manufactured by Seikagaku Corporation, Heparitinase (Code#: 100703) 8 mU/mL; filter-sterilized with a 0.22-μm filter) was added, followed by incubation at 37° C. for 6 hours. The plate was washed 3 times with 0.1% rHSA/PBS. The lacking of the heparan sulfate chains of perlecan domain 1 after heparitinase treatment of the plate was confirmed by immunostaining using an anti-heparan sulfate antibody (Ab Heparan Sulfate, purified (clone F58-10E4) Mouse IgM, κ-chain; AMS Biotechnology) as a primary antibody and Alexa Fluor 488 Goat Anti-Mouse IgM μ-chain (Invitrogen) as a secondary antibody.

(5) Pre-Culture of hiPS Cells

Pre-culture was performed in the same manner as in Example (3) using the LN421E8-coated plate, the P-421E8 (D1; a-C)-coated plate and the heparitinase-treated P-421E8 (D1; a-C)-coated plate.

(6) Induced Differentiation into Skeletal Muscle Cells

Induced differentiation into skeletal muscle cells was performed in the same manner as in Example 2 (4) using the LN421E8-coated plate, the P-421E8 (D1; a-C)-coated plate and the heparitinase-treated P-421E8 (D1; a-C)-coated plate.

(7) Immunostaining

Immunostaining was performed in the same manner as in Example 2 (5).

(8) Quantification of Gene Expression Level

The cells on the 14th day of differentiation were harvested, and the gene expression level of the dermomyotome marker SIX1 was quantified. The quantification of the gene expression level was performed in the same manner as in Example 2 (6).

Results (1) Immunostaining

Figure 13:
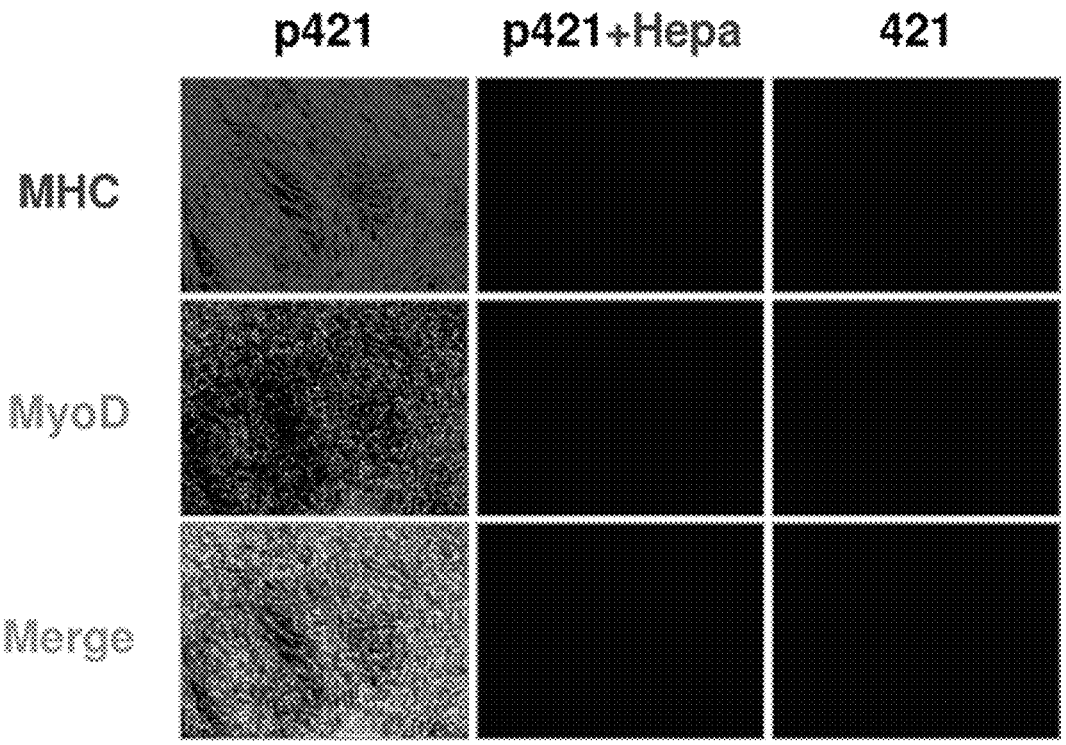
FIG. 13 shows the expression of myosin heavy chain (MHC) and MyoD examined by immunostaining in the cells on the 38th day of induced differentiation of human iPS cells (201B7 cell line) into skeletal muscle cells. The left column shows the results for the cells on a plate coated with a conjugate in which human perlecan domain 1 is fused to the α4 chain C-terminus of a human laminin α4β2γ1 E8 fragment. The middle column shows the results for the cells on a plate prepared by coating with a conjugate in which human perlecan domain 1 is fused to the α4 chain C-terminus of a human laminin α4β2γ1 E8 fragment and subsequent heparitinase treatment for removal of heparan sulfate chains. The right column shows the results for the cells on a plate coated with a human laminin α4β2γ1 E8 fragment.

The expression of MHC and MyoD examined by immunostaining in the cells on the 38th day are shown in FIG. 13. On the P-421E8 (D1; a-C)-coated plate (left: p421), MHC-positive cells and MyoD-positive cells were observed in the entire field of view. In contrast, on the heparitinase-treated P-421E8(D1; a-C)-coated plate (middle: p421+Hepa), neither MHC-positive cells nor MyoD-positive cells were observed, as was the case on the LN421E8-coated plate (right: 421).

(2) Gene Expression

Figure 14:
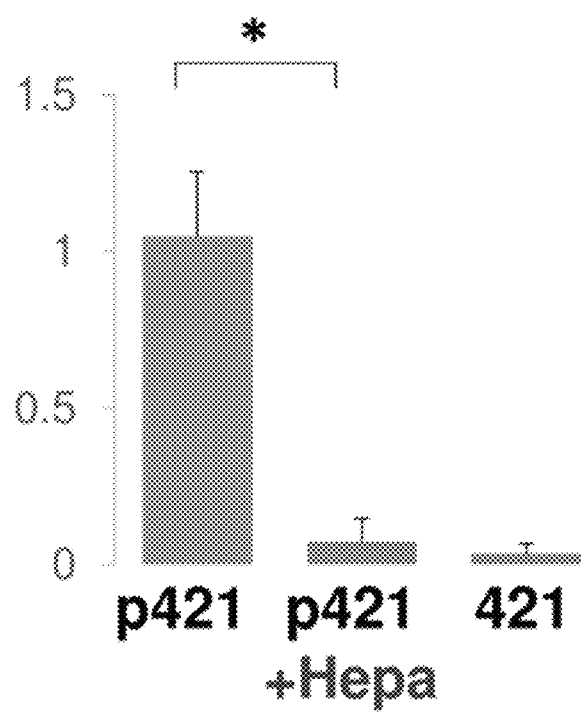
FIG. 14 shows the quantified expression level of the SIX1 gene in the cells on the 14th day of induced differentiation into skeletal muscle cells from human iPS cells (201B7 cell line) on a plate coated with a conjugate in which human perlecan domain 1 is fused to the α4 chain C-terminus of a human laminin α4β2γ1 E8 fragment; a plate prepared by coating with a conjugate in which human perlecan domain 1 is fused to the α4 chain C-terminus of a human laminin α4β2γ1 E8 fragment and subsequent heparitinase treatment for removal of heparan sulfate chains; or a plate coated with a human laminin α4β2γ1 E8 fragment.

The quantified expression level of the SIX1 gene in the cells on the 14th day is shown in FIG. 14. The SIX1 gene expression level in the cells on the heparitinase-treated P-421E8(D1; a-C)-coated plate (p421+Hepa) was as low as that in the cells on the LN421E8-coated plate (421). In contrast, the SIX1 gene expression level in the cells on the P-421E8(D1; a-C)-coated plate was significantly higher.

(3) Summary

The above results show that the heparan sulfate chains of perlecan domain 1 play an important role in the method for inducing pluripotent stem cells to differentiate into somatic cells using the conjugate of laminin E8 and perlecan domain 1.

Example 5

Examination of the usefulness of a conjugate of laminin E8 and perlecan domain 1 in induced differentiation of human iPS cells into vascular endothelial cells Experimental Materials and Methods (1) Laminin E8s and Conjugate of Laminin E8 and Perlecan Domain 1

Human laminin 411E8 (hereinafter referred to as "LN411E8"), a conjugate in which human perlecan domain 1 was fused to the α4 chain C-terminus of LN411E8 (hereinafter referred to as "P-411E8(D1; a-C)"); and LN511E8 were used. The LN511E8 was prepared as previously described by Ido et al. (Hiroyuki Ido et al., J. Biol. Chem., 282, 11144-11154, 2007) (see Examples in WO 2014/199754 A1). The LN411E8 was prepared as previously described by Ido et al. (loc. cit.) except for using α4 chain E8 instead of α5 chain E8. The P-411E8(D1; a-C) was prepared as in the preparation method of P-511E8(D1; a-C) described in WO 2014/199754 A1 (see Example 1) except for using α4 chain E8 instead of α5 chain E8.

(2) hiPS Cells hiPS cell line 409B2, which was received from Professor Nobuya Yamanaka from Kyoto University, was used.

(3) Plate Coating

The LN511E8, LN411E8 and P-411E8(D1; a-C) were separately dissolved in PBS(−) to prepare coating solutions. The coating solutions were added to the wells of 6-well culture plates (BD Falcon) at a coating concentration of 0.4 μg/cm$^2$, and the plates were allowed to stand at 37° C. for 2 hours to achieve coating.

(4) Induced Differentiation into Vascular Endothelial Cells

A cell detachment solution (TrypLE Select (Life Technologies) diluted 1:1 with 0.5 mM EDTA/PBS(−)) was added to the hiPS cells maintained, and after incubation at 37° C. for 5 minutes, the hiPS cells were detached. The hiPS cell populations were seeded at a density of 5 cell aggregation/cm$^2$ on the 6-well plate coated with LN511E8 and cultured in mTeSR1 medium. When the diameter of the colony reached about 750 μm, the culture medium was replaced with Essential 8 medium (Thermo Fisher) supplemented with CHIR99021 (4 μM), BMP4 (80 ng/mL) and VEGF (80 ng/mL) to induce differentiation into mesodermal progenitor cells.

After 51 hours from the medium replacement, treatment with TrypLE Express was performed at 37° C. for 20 minutes. All the cells were detached and dissociated into single cells by repeated pipetting. The mesodermal progenitor cells dissociated as single cells were seeded on the 6-well plate coated with LN411E8 or P-411E8(D1; a-C) at a density of $2\times10^5$/well. The cells were cultured in StemPro-34 SFM medium (Thermo Fisher) supplemented with VEGF (20 μg/mL or 80 μg/mL) for 4 days.

(5) FACS Analysis

The marker expression on the 4th day of induced differentiation into vascular endothelial cells was analyzed by flow cytometry. More specifically, the cells were treated with TrypLE Express at 37° C. for 20 minutes and then allowed to react with appropriate antibodies in StemPro-34 SFM medium. The antibodies used were an anti-human VE-cadherin antibody (1:100 dilution, eBioscience) and an anti-human CD31 antibody (1:10 dilution, R&D systems).

Results (1) Number of Vascular Endothelial Cells
(VE-Cadherin-Positive/CD31-Positive Cells)

Figure 15:
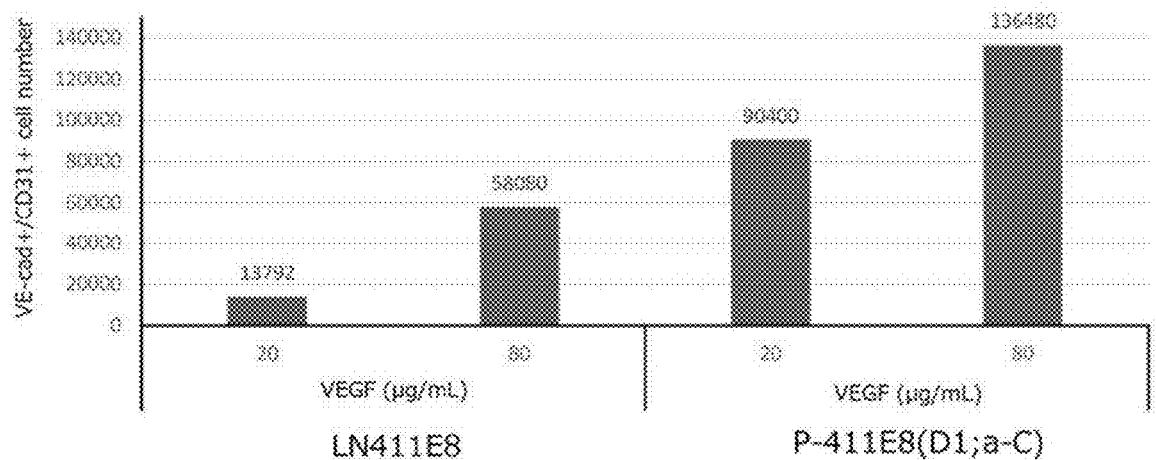
FIG. 15 shows the number of VE-cadherin-positive/CD31 positive-cells determined by FACS analysis of the cells on the 4th day of induced differentiation of human iPS cells (201B7 cell line) into vascular endothelial cells. The two left bars show the results for the cells on a plate coated with a human laminin α4β1γ1 E8 fragment. The two right bars show the results for the cells on a plate coated with a conjugate in which human perlecan domain 1 is fused to the α4 chain C-terminus of a human laminin α4β1γ1 E8 fragment.

The results are shown in FIG. 15. At both of the VEGF concentrations, the number of VE-cadherin-positive/CD31 positive-cells on the P-411E8(D1; a-C)-coated plate was significantly greater than that on the LN411E8-coated plate.

(2) Fraction of Vascular Endothelial Cells
(VE-Cadherin-Positive/CD31-Positive Cells)

Figure 16:
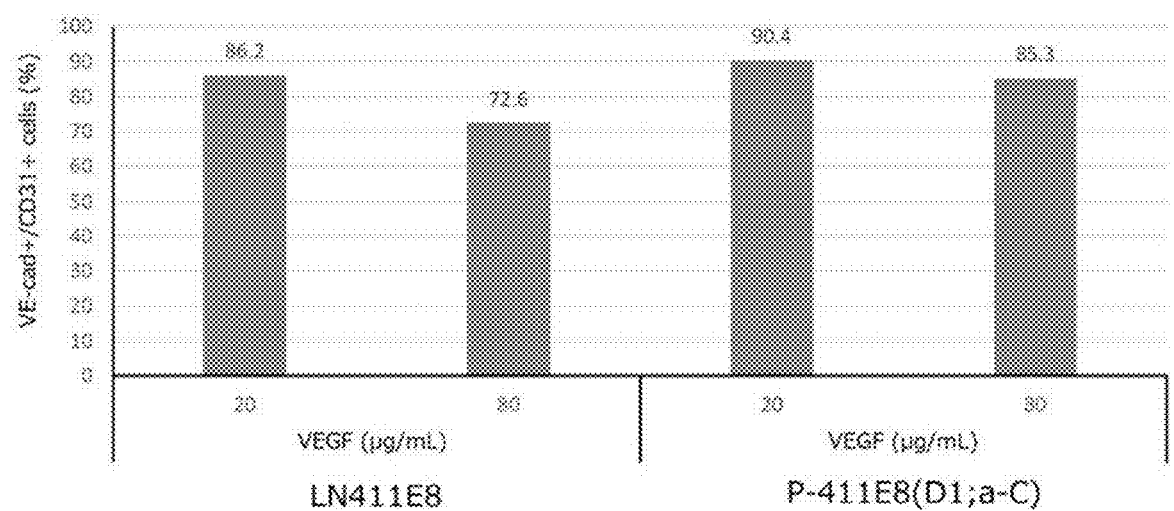
FIG. 16 shows the fraction of VE-cadherin-positive/CD31 positive-cells determined by FACS analysis of the cells on the 4th day of induced differentiation of human iPS cells (201B7 cell line) into vascular endothelial cells. The two left bars show the results for the cells on a plate coated with a human laminin α4β1γ1 E8 fragment. The two right bars show the results for the cells on a plate coated with a conjugate in which human perlecan domain 1 is fused to the α4 chain C-terminus of a human laminin α4β1γ1 E8 fragment.

The results are shown in FIG. 16. At both of the VEGF concentrations, the fraction of VE-cadherin-positive/CD31 positive-cells on the P-411E8(D1; a-C)-coated plate tended to be higher than that on the LN411E8-coated plate.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for inducing pluripotent stem cells to differentiate into somatic cells, the method comprising bringing pluripotent stem cells into contact with a conjugate of a laminin E8 fragment and a growth factor binding domain-containing fragment of a heparan sulfate proteoglycan in a culture medium containing a heparin binding growth factor and a canonical Wnt signal activator,
    wherein the somatic cells are mesoderm-derived somatic cells, and
    wherein the heparin binding growth factor is one or more selected from the group consisting of bone morphogenetic protein 4, activin A, basic fibroblast growth factor, hepatocyte growth factor and vascular endothelial growth factor.

2. The method according to claim 1, wherein the growth factor binding domain-containing fragment of a heparan sulfate proteoglycan is a perlecan domain 1-containing fragment.

3. The method according to claim 1, wherein the conjugate has a structure in which the growth factor binding domain-containing fragment of a heparan sulfate proteoglycan is conjugated to the α chain C-terminus of the laminin E8 fragment.

4. The method according to claim 1, wherein the method comprises using a cell culture vessel coated with the conjugate for inducing pluripotent stem cells to differentiate into somatic cells.

5. The method according to claim 1, wherein the pluripotent stem cells are human iPS cells.

6. The method according to claim 5, wherein human iPS cells are induced to differentiate into cardiomyocytes in a culture medium containing bone morphogenetic protein 4 or activin A, and wherein cells are brought into contact with a conjugate in which perlecan domain 1 is conjugated to the α chain C-terminus of a human laminin α4β2γ1 E8 fragment or the α chain C-terminus of a human laminin α5β1γ1 E8 fragment.

7. The method according to claim 5, wherein human iPS cells are induced to differentiate into skeletal muscle cells in a culture medium containing basic fibroblast growth factor and hepatocyte growth factor, and wherein cells are brought into contact with a conjugate in which perlecan domain 1 is conjugated to the α chain C-terminus of a human laminin α4β2γ1 E8 fragment, the α chain C-terminus of a human laminin α5β1γ1 E8 fragment, the α chain C-terminus of a human laminin α4β1γ1 E8 fragment, or the α chain C-terminus of a human laminin α5β2γ1 E8 fragment.

8. The method according to claim 5, wherein human iPS cells are induced to differentiate into vascular endothelial cells in a culture medium containing vascular endothelial growth factor, and wherein cells are brought into contact with a conjugate in which perlecan domain 1 is conjugated to the α chain C-terminus of a human laminin α4β1γ|E8 fragment.

9. The method according to claim 1, wherein the canonical Wnt signal activator is CHIR99021.

* * * * *